(12) United States Patent
Badruddin et al.

(10) Patent No.: US 11,974,754 B2
(45) Date of Patent: May 7, 2024

(54) SYSTEMS AND METHODS FOR TREATING ANEURYSMS

(71) Applicant: Galaxy Therapeutics, Inc., Milpitas, CA (US)

(72) Inventors: Aamir Badruddin, Bolingbrook, IL (US); Thomas J. Wolfe, Shorewood, WI (US); Osama O. Zaidat, Lambertville, MI (US); Edgard Luiz Ramos Pereira, Boca Raton, FL (US); Arturo Rosqueta, San Jose, CA (US); Brett Follmer, Santa Clara, CA (US)

(73) Assignee: Galaxy Therapeutics, Inc., Milpitas, CA (US)

( * ) Notice: Subject to any disclaimer, the term of this patent is extended or adjusted under 35 U.S.C. 154(b) by 436 days.

(21) Appl. No.: 17/222,092

(22) Filed: Apr. 5, 2021

(65) Prior Publication Data
US 2021/0219982 A1 Jul. 22, 2021

Related U.S. Application Data

(63) Continuation of application No. 17/084,285, filed on Oct. 29, 2020, now Pat. No. 11,033,277, which is a
(Continued)

(51) Int. Cl.
*A61F 2/01* (2006.01)
*A61B 17/00* (2006.01)
(Continued)

(52) U.S. Cl.
CPC .. *A61B 17/12113* (2013.01); *A61B 17/00234* (2013.01); *A61B 17/12031* (2013.01);
(Continued)

(58) Field of Classification Search
CPC ........ A61B 17/12113; A61B 17/12177; A61B 2017/00867; A61B 17/00; A61B 17/12;
(Continued)

(56) References Cited

U.S. PATENT DOCUMENTS

| 5,250,071 A | 10/1993 | Palermo |
| 5,282,806 A | 2/1994 | Haber et al. |

(Continued)

FOREIGN PATENT DOCUMENTS

| CN | 102871700 B | 4/2015 |
| CN | 103006285 B | 6/2015 |

(Continued)

OTHER PUBLICATIONS

Shapiro, M., Raz, E., Becske, T., Nelson, P., "Variable Porosity of the Pipeline Embolization Device in Straight and Curved Vessels: A Guide for Optimal Deployment Strategy", Original Research Interventional, Sep. 26, 2013, 6 pages, 10.3174/ajnr.A3742, American Society of Neuroradiology, Oak Brook, USA.

(Continued)

*Primary Examiner* — Vi X Nguyen
(74) *Attorney, Agent, or Firm* — BLAIR WALKER IP SERVICES, LLC

(57) ABSTRACT

A vaso-occlusive system configured for embolizing an aneurysm, includes an implantable vaso-occlusive device coupled to a distal end of an elongate pusher and having a collapsed delivery configuration and an expanded, deployed configuration, wherein the vaso-occlusive device includes a proximal end configured to seat against the aneurysm adjacent the neck of the aneurysm, a distal end configured to extend in the sac and away from the neck of the aneurysm, and a central longitudinal axis, and wherein the vaso-occlusive device is configured to be releasably coupled to the distal end of the pusher at a releasable joint including
(Continued)

either one or both of the configurations in the list consisting of: (1) the distal end of the pusher extends from the releasable joint at an angle formed with the central longitudinal axis of between about 30 degrees and about 120 degrees, and (2) the releasable joint is coupled at a location on the proximal end of the vaso-occlusive device that is radially offset from the central longitudinal axis.

20 Claims, 12 Drawing Sheets

Related U.S. Application Data continuation of application No. 16/840,412, filed on Apr. 5, 2020, now Pat. No. 10,856,880.

(60) Provisional application No. 62/975,741, filed on Feb. 12, 2020, provisional application No. 62/975,744, filed on Feb. 12, 2020, provisional application No. 62/914,442, filed on Oct. 12, 2019, provisional application No. 62/852,988, filed on May 25, 2019.

(51) Int. Cl.
*A61B 17/12* (2006.01)
*A61B 90/00* (2016.01)

(52) U.S. Cl.
CPC .. *A61B 17/12172* (2013.01); *A61B 17/12177* (2013.01); *A61B 2017/00867* (2013.01); *A61B 2017/1205* (2013.01); *A61B 2017/12054* (2013.01); *A61B 2017/12059* (2013.01); *A61B 2017/12063* (2013.01); *A61B 2017/12068* (2013.01); *A61B 2090/3966* (2016.02)

(58) Field of Classification Search
CPC ........ A61B 17/12172; A61B 17/12031; A61B 17/00234; A61F 2/01; A61F 2/013; A61F 2002/011
See application file for complete search history.

(56) References Cited

U.S. PATENT DOCUMENTS

| | | | |
|---|---|---|---|
| 5,304,195 A | 4/1994 | Twyford, Jr. et al. | |
| 5,556,390 A | 9/1996 | Hicks | |
| 5,795,331 A | 8/1998 | Cragg et al. | |
| 5,935,148 A | 8/1999 | Villar et al. | |
| 6,086,577 A | 7/2000 | Ken et al. | |
| 6,093,199 A | 7/2000 | Brown et al. | |
| 6,152,144 A | 11/2000 | Lesh et al. | |
| 6,391,037 B1 | 5/2002 | Greenhalgh | |
| 6,454,780 B1 | 9/2002 | Wallace | |
| 6,506,204 B2 | 1/2003 | Mazzochi | |
| 6,544,163 B2 | 4/2003 | Wallace et al. | |
| 6,613,074 B1 | 9/2003 | Mitelberg et al. | |
| 6,936,055 B1 | 8/2005 | Ken et al. | |
| 6,994,689 B1 | 2/2006 | Zadno-Azizi et al. | |
| 7,128,736 B1 | 10/2006 | Abrams et al. | |
| 7,195,636 B2 | 3/2007 | Avellanet et al. | |
| 7,229,461 B2 | 6/2007 | Chin et al. | |
| 7,367,985 B2 * | 5/2008 | Mazzocchi ...... A61B 17/12109 606/191 | |
| 7,410,482 B2 | 8/2008 | Murphy et al. | |
| 7,569,066 B2 | 8/2009 | Gerberding et al. | |
| 7,749,242 B2 | 7/2010 | Tran et al. | |
| 8,142,456 B2 | 3/2012 | Rosqueta et al. | |
| 8,333,796 B2 | 12/2012 | Tompkins et al. | |
| 8,388,650 B2 | 3/2013 | Gerberding et al. | |
| 8,398,670 B2 | 3/2013 | Amplatz et al. | |
| 8,551,132 B2 | 10/2013 | Eskridge et al. | |
| 8,597,320 B2 | 12/2013 | Sepetka et al. | |
| 8,728,117 B1 | 5/2014 | Janardhan et al. | |
| 8,777,979 B2 | 7/2014 | Shrivastava et al. | |
| 8,820,207 B2 | 9/2014 | Marchand et al. | |
| 8,826,791 B2 | 9/2014 | Thompson et al. | |
| 8,864,790 B2 | 10/2014 | Strauss et al. | |
| 8,864,791 B2 | 10/2014 | Bloom et al. | |
| 8,940,015 B2 | 1/2015 | Kariniemi | |
| 8,998,947 B2 | 4/2015 | Aboytes et al. | |
| 9,107,670 B2 | 8/2015 | Hannes et al. | |
| 9,113,890 B2 | 8/2015 | Dasnukar et al. | |
| 9,198,668 B2 | 12/2015 | Theobald et al. | |
| 9,259,337 B2 | 2/2016 | Cox et al. | |
| 9,314,326 B2 | 4/2016 | Wallace et al. | |
| 9,510,811 B2 | 12/2016 | Akpinar | |
| 9,585,670 B2 | 3/2017 | Hines | |
| 9,597,087 B2 | 3/2017 | Marchand et al. | |
| 9,636,117 B2 | 5/2017 | Bachman et al. | |
| 9,669,188 B2 | 6/2017 | Echarri et al. | |
| 9,855,052 B2 | 1/2018 | Aboytes et al. | |
| 9,918,720 B2 | 3/2018 | Marchand et al. | |
| 9,980,733 B2 | 5/2018 | Badruddin et al. | |
| 10,111,670 B2 | 10/2018 | Lorenzo et al. | |
| 10,123,805 B2 | 11/2018 | Ayres et al. | |
| 10,136,896 B2 | 11/2018 | Hewitt et al. | |
| 10,149,676 B2 | 12/2018 | Mirigian et al. | |
| 10,478,195 B2 | 11/2019 | Aboytes et al. | |
| 10,751,065 B2 | 8/2020 | Soto del Valle et al. | |
| 11,278,292 B2 | 3/2022 | Gorochow et al. | |
| 11,413,046 B2 | 8/2022 | Xu et al. | |
| 11,497,504 B2 | 11/2022 | Xu et al. | |
| 11,583,282 B2 | 2/2023 | Gorochow et al. | |
| 11,596,412 B2 | 3/2023 | Xu et al. | |
| 11,602,350 B2 | 3/2023 | Gorochow et al. | |
| 2002/0169473 A1 | 11/2002 | Sepetka et al. | |
| 2002/0188314 A1 | 12/2002 | Anderson et al. | |
| 2003/0171770 A1 | 9/2003 | Kusleika et al. | |
| 2003/0176884 A1 | 9/2003 | Berrada et al. | |
| 2003/0195553 A1 | 10/2003 | Wallace et al. | |
| 2004/0034386 A1 | 2/2004 | Fulton et al. | |
| 2004/0044391 A1 | 3/2004 | Porter | |
| 2004/0172056 A1 | 9/2004 | Guterman et al. | |
| 2004/0199201 A1 | 10/2004 | Kellett et al. | |
| 2005/0033409 A1 | 2/2005 | Burke et al. | |
| 2005/0107823 A1 | 5/2005 | Leone et al. | |
| 2005/0171478 A1 | 8/2005 | Selmon et al. | |
| 2005/0277978 A1 | 12/2005 | Greenhalgh | |
| 2006/0064151 A1 | 3/2006 | Guterman et al. | |
| 2006/0106417 A1 | 5/2006 | Tessmer et al. | |
| 2006/0155323 A1 | 7/2006 | Porter et al. | |
| 2007/0173928 A1 | 7/2007 | Morsi | |
| 2007/0208376 A1 | 9/2007 | Meng | |
| 2007/0225794 A1 | 9/2007 | Thramann et al. | |
| 2007/0270902 A1 | 11/2007 | Slazas et al. | |
| 2008/0045997 A1 | 2/2008 | Balgobin et al. | |
| 2008/0097495 A1 | 4/2008 | Feller, III et al. | |
| 2008/0147100 A1 | 6/2008 | Wallace | |
| 2008/0281350 A1 | 11/2008 | Sepetka et al. | |
| 2008/0319533 A1 | 12/2008 | Lehe | |
| 2009/0062841 A1 | 3/2009 | Amplatz et al. | |
| 2009/0082803 A1 | 3/2009 | Adams et al. | |
| 2009/0099647 A1 | 4/2009 | Glimsdale et al. | |
| 2009/0177261 A1 | 7/2009 | Teoh et al. | |
| 2009/0264978 A1 | 10/2009 | Dieck et al. | |
| 2009/0287291 A1 | 11/2009 | Becking et al. | |
| 2009/0318941 A1 | 12/2009 | Sepetka et al. | |
| 2010/0179583 A1 | 7/2010 | Carpenter et al. | |
| 2011/0046719 A1 | 2/2011 | Frid | |
| 2011/0202085 A1 | 8/2011 | Loganathan et al. | |
| 2012/0065667 A1 | 3/2012 | Javois et al. | |
| 2012/0071911 A1 | 3/2012 | Sadasivan et al. | |
| 2012/0143317 A1 | 6/2012 | Cam et al. | |
| 2012/0259244 A1 | 10/2012 | Roberts et al. | |
| 2012/0283768 A1 | 11/2012 | Cox et al. | |
| 2012/0303052 A1 | 11/2012 | Connor | |
| 2012/0310270 A1 | 12/2012 | Murphy et al. | |
| 2012/0330347 A1 | 12/2012 | Becking et al. | |
| 2013/0066357 A1 | 3/2013 | Abotes et al. | |
| 2013/0073026 A1 | 3/2013 | Russo et al. | |
| 2013/0190800 A1 | 7/2013 | Murphy et al. | |

(56) References Cited

U.S. PATENT DOCUMENTS

| | | | |
|---|---|---|---|
| 2013/0211495 A1* | 8/2013 | Halden | A61B 17/12109 623/1.12 |
| 2014/0005714 A1 | 1/2014 | Quick et al. | |
| 2014/0012303 A1 | 1/2014 | Heipl | |
| 2014/0052233 A1 | 2/2014 | Cox et al. | |
| 2014/0172001 A1 | 6/2014 | Becking et al. | |
| 2014/0257360 A1 | 9/2014 | Keillor | |
| 2014/0343602 A1 | 11/2014 | Cox et al. | |
| 2015/0005811 A1 | 1/2015 | Lubock et al. | |
| 2015/0133989 A1 | 5/2015 | Lubock et al. | |
| 2015/0250628 A1 | 9/2015 | Monstadt et al. | |
| 2015/0272589 A1 | 10/2015 | Lorenzo | |
| 2015/0313605 A1 | 11/2015 | Griffin | |
| 2016/0022445 A1 | 1/2016 | Ruvalcava et al. | |
| 2016/0030050 A1 | 2/2016 | Franano et al. | |
| 2016/0120551 A1 | 5/2016 | Connor | |
| 2016/0278749 A1 | 9/2016 | Javois et al. | |
| 2016/0317277 A1 | 11/2016 | Carpenter et al. | |
| 2017/0014114 A1 | 1/2017 | Radfiee et al. | |
| 2017/0156734 A1 | 6/2017 | Griffin | |
| 2017/0224350 A1 | 8/2017 | Shimizu et al. | |
| 2017/0224355 A1 | 8/2017 | Bowman et al. | |
| 2017/0348014 A1 | 12/2017 | Wallace et al. | |
| 2017/0367708 A1 | 12/2017 | Mayer et al. | |
| 2017/0367713 A1 | 12/2017 | Greene, Jr. et al. | |
| 2018/0036012 A1 | 2/2018 | Aboytes et al. | |
| 2018/0049731 A1 | 2/2018 | Hardy et al. | |
| 2018/0242979 A1 | 8/2018 | Lorenzo | |
| 2019/0053810 A1 | 2/2019 | Griffin | |
| 2019/0110796 A1 | 4/2019 | Jayaraman | |
| 2019/0192167 A1 | 6/2019 | Lorenzo | |
| 2019/0192168 A1 | 6/2019 | Lorenzo | |
| 2019/0223876 A1 | 7/2019 | Badruddin et al. | |
| 2019/0223881 A1 | 7/2019 | Hewitt et al. | |
| 2019/0357914 A1 | 11/2019 | Gorochow et al. | |
| 2020/0113576 A1 | 4/2020 | Gorochow et al. | |
| 2020/0367900 A1 | 11/2020 | Pedroso et al. | |
| 2020/0367906 A1 | 11/2020 | Xu et al. | |
| 2021/0275184 A1 | 9/2021 | Hewitt et al. | |
| 2022/0125567 A1 | 4/2022 | Center et al. | |
| 2022/0202425 A1 | 6/2022 | Gorochow et al. | |
| 2022/0304699 A1 | 9/2022 | Gorochow | |
| 2023/0017191 A1 | 1/2023 | Gorochow et al. | |

FOREIGN PATENT DOCUMENTS

| | | |
|---|---|---|
| DE | 102012016555 A1 | 2/2014 |
| DE | 102013006503 A1 | 7/2014 |
| EP | 0832607 A1 | 4/1998 |
| EP | 3146916 A1 | 3/2017 |
| EP | 2647343 B1 | 7/2017 |
| WO | WO1999/05977 A1 | 2/1999 |
| WO | WO2002/00139 A1 | 1/2002 |
| WO | WO2005/107650 A2 | 11/2005 |
| WO | WO2009/132045 A2 | 10/2009 |
| WO | WO2013/138615 A2 | 9/2013 |
| WO | WO2017/102804 A1 | 6/2017 |
| WO | WO2017/153603 A1 | 9/2017 |
| WO | WO2017/220400 A1 | 12/2017 |
| WO | WO2019038293 A1 | 2/2019 |

OTHER PUBLICATIONS

Perez, M., Henkes, H., Bouillot, P., Brina, O., Slater, L., Pereira, V., "Intra-aneurysmal hemodynamics: evaluation of pCONus and pCANvas bifurcation aneurysm devices using DSA optical flow imaging", Journal of NeuroInterventional Surgery, Dec. 23, 2015, 6 pages, 10.1136/neurintsurg-2015-011927, Society of NeuroInterventional Surgery, Fairfax, USA.

Torii, R., Oshima, M., Kobayashi, T., Takagi, K., Tezduyar, T., "Fluid-structure interaction modeling of a patient-specific cerebral aneurysm: influence of structural modeling." Computational Mechanics 43: 151-159 (2008).

Control, etc. http://www.asianjns.org/articles/2012/7/4/images/AsianJNeurosurg_2012_7_4_159_106643_f7.jpg downloaded from internet Apr. 3, 2020.

Cerus https://neuronewsinternational-wpengine.netdna-ssl.com/wp-content/uploads/sites/3/2016/07/Cerus-Endovascular-Contour-300x194.jpg downloaded from internet Apr. 3, 2020.

Contour https://neuronewsinternational-wpengine.netdna-ssl.com/wp-content/uploads/sites/3/2017/06/Contour-e1497957260381-300x194.png downloaded from internet Apr. 3, 2020.

Medtronic https://evtoday.com/images/articles/2017-02/0217-endovascular-fig1.png downloaded from internet Apr. 3, 2020.

Bhogal, P., Udani, S., Cognard, C., Piotin, M., Brouwer, P., Sourour, N., Andersson, T., Makalanda, L., Wong, K., Fiorella, D., Arthur, A., Yeo, L., Soderman, M., Henkes, H., Pierot, L., "Endovascular flow disruption: where are we now?" Journal of Neurointerventional Surgery 11: 1024-1035 (2019).

\* cited by examiner

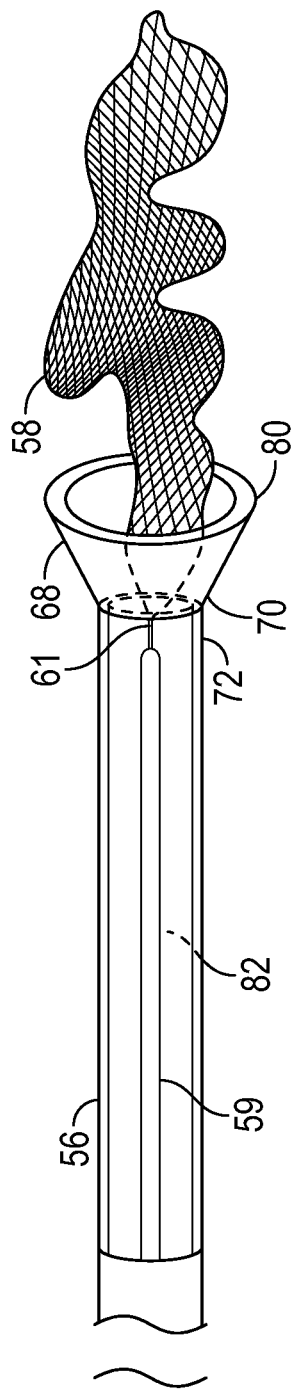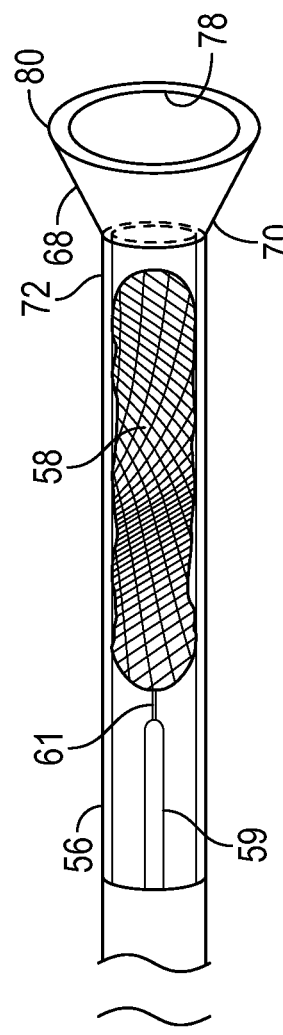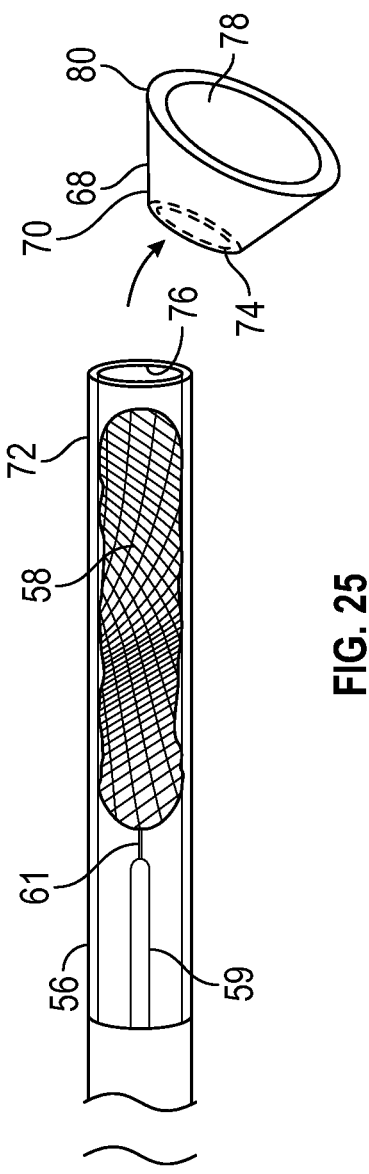
FIG. 23
FIG. 24
FIG. 25

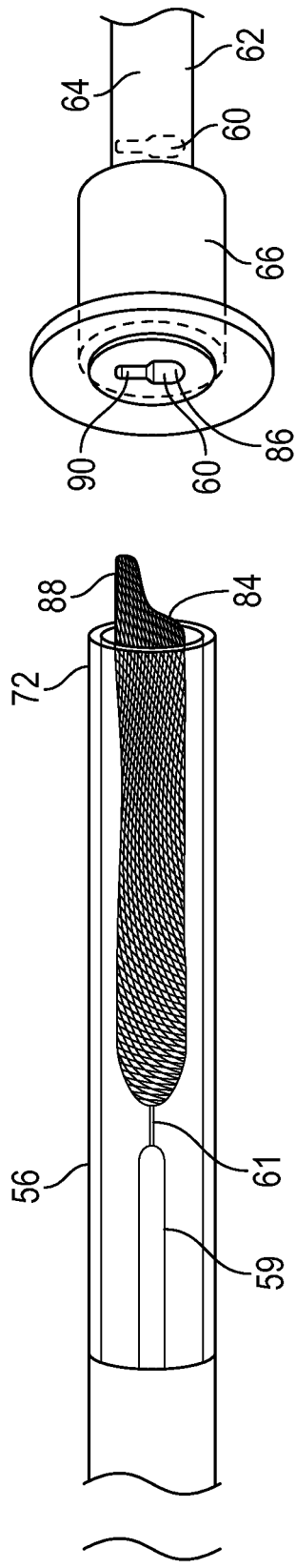
FIG. 26
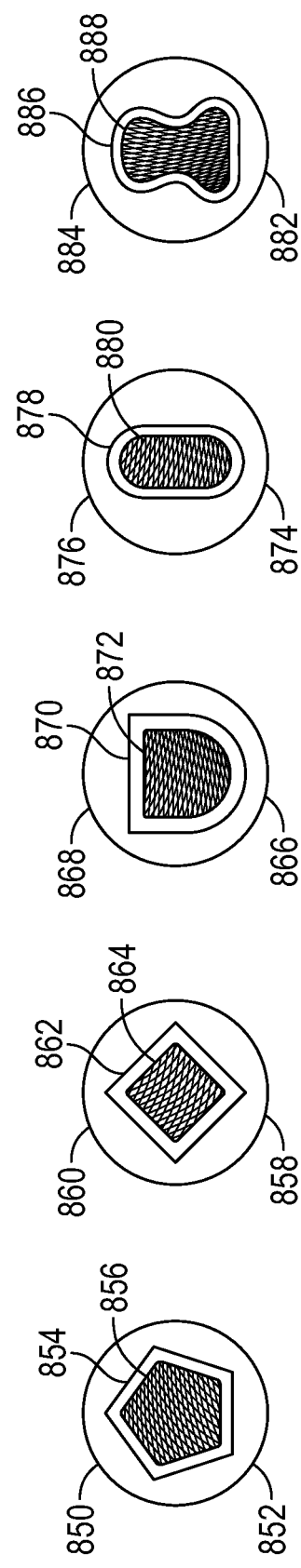
FIG. 27A
FIG. 27B
FIG. 27C
FIG. 27D
FIG. 27E

SYSTEMS AND METHODS FOR TREATING ANEURYSMS

INCORPORATION BY REFERENCE TO ANY PRIORITY APPLICATIONS

This application is a continuation of U.S. patent application Ser. No. 17/084,285, filed on Oct. 29, 2020, now U.S. Pat. No. 11,033,277, which is a continuation of U.S. patent application Ser. No. 16/840,412, filed on Apr. 5, 2020, now U.S. Pat. No. 10,856,880, which claims the benefit of priority to U.S. Provisional Patent Application No. 62/852,988, filed on May 25, 2019, U.S. Provisional Patent Application No. 62/914,442, filed on Oct. 12, 2019, U.S. Provisional Patent Application No. 62/975,741, filed on Feb. 12, 2020, and U.S. Provisional Patent Application No. 62/975,744, filed on Feb. 12, 2020, all of which are herein incorporated by reference in their entirety for all purposes. Priority is claimed pursuant to 35 U.S.C. § 120 and 35 U.S.C. § 119.

BACKGROUND OF THE INVENTION

Field of the Invention

The field of the invention generally relates to embolic devices for filling spaces in the vascular system, including cerebral aneurysms or left atrial appendages. In some case, the embolic devices may be used to embolize native vessels.

Description of the Related Art

An embolic device may be used as a stand-alone device to occlude and aneurysm, or may be used with an adjunctive device or material.

SUMMARY OF THE INVENTION

In one embodiment of the present disclosure, a vaso-occlusive system configured for embolizing an aneurysm, the aneurysm having a neck and a sac, the system including an elongate pusher configured to be slidably disposed within a delivery catheter, the delivery catheter having a proximal end, a distal end, and a delivery lumen extending therebetween, an implantable vaso-occlusive device coupled to a distal end of the pusher, the vaso-occlusive device configured for implantation in the aneurysm sac and having a collapsed delivery configuration when restrained within the delivery lumen of the delivery catheter, and an expanded, deployed configuration after being delivered out of the delivery lumen of the delivery catheter and into the aneurysm sac, wherein the vaso-occlusive device includes a proximal face configured to seat against a lower wall portion of the sac of the aneurysm against the neck of the aneurysm and a concavity, opposite the proximal face, and having a perimeter extending into the sac and away from the neck of the aneurysm, the concavity arranged around a longitudinal axis, and wherein the vaso-occlusive device is configured to be releasably coupled to the distal end of the pusher at a releasable joint, the distal end of the pusher extending from the releasable joint at an angle formed with the central longitudinal axis of between about 30 degrees and about 120 degrees.

In another embodiment of the present disclosure, a vaso-occlusive system configured for embolizing an aneurysm, the aneurysm having a neck and a sac, the system including an elongate pusher configured to be slidably disposed within a delivery catheter, the delivery catheter having a proximal end, a distal end, and a delivery lumen extending therebetween, an implantable vaso-occlusive device coupled to a distal end of the pusher, the vaso-occlusive device configured for implantation in the aneurysm sac and having a collapsed delivery configuration when restrained within the delivery lumen of the delivery catheter, and an expanded, deployed configuration after being delivered out of the delivery lumen of the delivery catheter and into the aneurysm sac, wherein the vaso-occlusive device includes a proximal face configured to seat against a lower wall portion of the sac of the aneurysm against the neck of the aneurysm and a concavity, opposite the proximal face, and having a perimeter extending into the sac and away from the neck of the aneurysm, the concavity arranged around a longitudinal axis, and wherein the vaso-occlusive device is configured to be releasably coupled to the distal end of the pusher at a releasable joint, and wherein the releasable joint is coupled at a location on the proximal face of the vaso-occlusive device that is radially offset from the central longitudinal axis.

In yet another embodiment of the present disclosure, a vaso-occlusive system configured for embolizing an aneurysm, the aneurysm having a neck and a sac, the system including an elongate pusher configured to be slidably disposed within a delivery catheter, the delivery catheter having a proximal end, a distal end, and a delivery lumen extending therebetween, an implantable vaso-occlusive device coupled to a distal end of the pusher, the vaso-occlusive device configured for implantation in the aneurysm sac and having a collapsed delivery configuration when restrained within the delivery lumen of the delivery catheter, and an expanded, deployed configuration after being delivered out of the delivery lumen of the delivery catheter and into the aneurysm sac, wherein the vaso-occlusive device includes a proximal face configured to seat against a lower wall portion of the sac of the aneurysm against the neck of the aneurysm and a concavity, opposite the proximal face, and having a perimeter extending into the sac and away from the neck of the aneurysm, the concavity arranged around a longitudinal axis, and wherein the vaso-occlusive device is configured to be releasably coupled to the distal end of the pusher at a releasable joint, and wherein the releasable joint has a characteristic chosen from the list consisting of: (1) the distal end of the pusher extends from the releasable joint at an angle formed with the central longitudinal axis of between about 30 degrees and about 120 degrees, and (2) the releasable joint is coupled at a location on the proximal face of the vaso-occlusive device that is radially offset from the central longitudinal axis.

In still another embodiment of the present disclosure, a system for embolizing an aneurysm includes an expandable implant configured for placement within an aneurysm, the implant having a collapsed configuration and an expanded configuration, the expanded configuration having an asymmetric shape in relation to a longitudinal axis, and a delivery catheter having a proximal end and a distal end and a lumen extending from the proximal end to the distal end, the lumen having a non-circular cross-section at least at a distal region adjacent the distal end of the delivery catheter, wherein expandable implant in its collapsed configuration is configured to fit into the lumen in the distal region in a keyed manner, such that the expandable implant is deliverable from the lumen at the distal end of the delivery catheter in a particular rotational position in relation to the longitudinal axis.

In yet another embodiment of the present disclosure, a method for inserting an expandable implant includes providing an introducer having a proximal end and a distal end and an introducer lumen extending between the proximal end of the introducer and the distal end of the introducer, the introducer lumen configured to hold an expandable implant in its collapsed configuration while the expandable implant is introduced into the lumen of the delivery catheter at its proximal end, wherein the lumen of the delivery catheter has a non-circular shape, and wherein the expandable implant in its collapsed configuration has a substantially non-circular shape, pushing the expandable implant out of the introducer lumen and into the lumen of the delivery catheter such that the substantially non-circular shape of the expandable implant in its collapsed configuration is oriented in a keyed manner with the non-circular shape of the lumen of the delivery catheter, and advancing the expandable implant such that it is entirely within the lumen of the delivery catheter.

In still another embodiment of the present disclosure, a vaso-occlusive system configured for embolizing an aneurysm, the aneurysm having a neck and a sac, the system includes an elongate pusher configured to be slidably disposed within a delivery catheter, the delivery catheter having a proximal end, a distal end, and a delivery lumen extending therebetween, an implantable vaso-occlusive device coupled to a distal end of the pusher, the vaso-occlusive device configured for implantation in the aneurysm sac and having a collapsed delivery configuration when restrained within the delivery lumen of the delivery catheter, and an expanded, deployed configuration after being delivered out of the delivery lumen of the delivery catheter and into the aneurysm sac, wherein the vaso-occlusive device includes a proximal end configured to seat against the aneurysm adjacent the neck of the aneurysm, a distal end configured to extend in the sac and away from the neck of the aneurysm, and a central longitudinal axis, and wherein the vaso-occlusive device is configured to be releasably coupled to the distal end of the pusher at a releasable joint, wherein the releasable joint includes either one or both of the configurations in the list consisting of: (1) the distal end of the pusher extends from the releasable joint at an angle formed with the central longitudinal axis of between about 30 degrees and about 120 degrees, and (2) the releasable joint is coupled at a location on the proximal end of the vaso-occlusive device that is radially offset from the central longitudinal axis.

BRIEF DESCRIPTION OF THE DRAWINGS

FIG. 23 is a perspective view of a loading sheath according to an embodiment of the present disclosure.

FIG. 24 is a perspective view of the loading sheath of FIG. 23 with an occlusion device restrained in its collapsed configuration.

FIG. 25 is a perspective view of the loading sheath of FIG. 23 being changed to another configuration.

FIG. 26 is a perspective of the loading sheath of FIG. 23 being used to load an occlusion device into a proximal end of a delivery catheter.

FIGS. 27A-27E are alternate configurations of the lumen of a delivery catheter, according to embodiments of the present disclosure.

DETAILED DESCRIPTION OF THE ILLUSTRATED EMBODIMENTS

Figure 1:
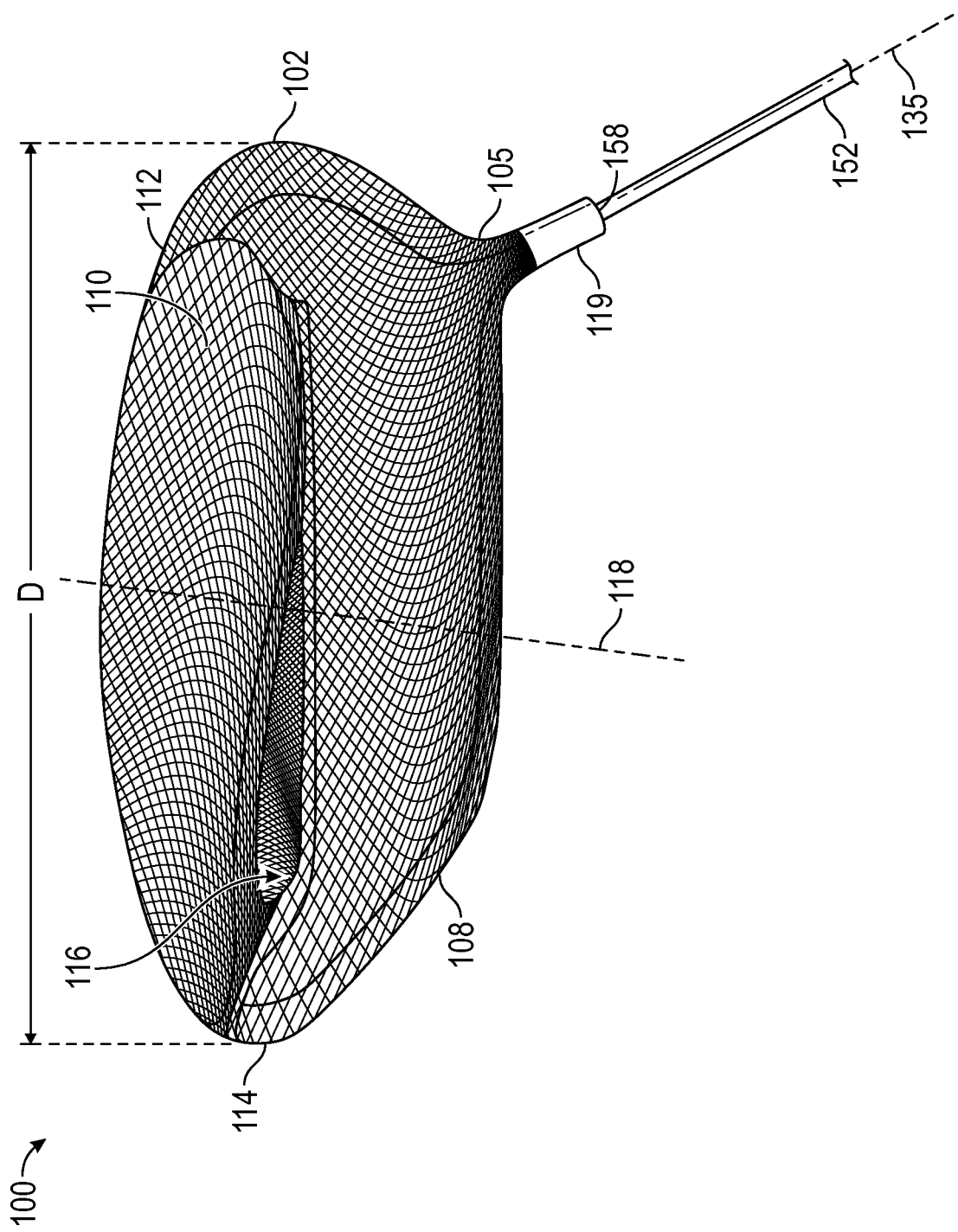
FIG. 1 is a perspective view of an occlusion device according to an embodiment of the present disclosure.

Aneurysms are abnormal bulging or weakening of a blood vessel, often an artery, and can have many complications. A bulging of the blood vessel can disrupt or put pressure on surrounding tissues. Cerebral aneurysms can result in a variety of side effects, such as impaired vision, impaired speech, impaired balance, etc. Further, the aneurysm creates a volume that is not along the main flow path of the blood through the blood vessel. It therefore can serve as a location for blood to become stagnant and, due to swirling eddy currents, can contribute to the formation of a thromboembolism. If an aneurysm ruptures, it can cause severe internal bleeding, which in cerebral arteries can often become fatal.

Aneurysms can be treated externally with open surgery. Such procedures typically involve closing off the entrance or "neck" of the aneurysm with a device such as vascular clip, clamp or a ligature. However, such open surgical procedures can be highly invasive and may lead to trauma to the adjacent tissue and other side effects.

Aneurysms can also be treated through endovascular procedures. In one procedure, detachable lengths of wires (e.g., coils) are inserted into the interior volume of the aneurysm using a catheter. The coils are intended to fill the volume of the aneurysm to decrease the flow of blood into the aneurysm, inducing stagnation of flow and stimulate clotting within the aneurysm. In settings of large cerebral aneurysms, filling of the aneurysm with multiple coils can lead to mass effect that may induce brain swelling and be an independent cause for new symptoms. In another procedure, for aneurysms with a relatively large neck, the adjunctive use of stents assists with the retention of the coils within the aneurysm. This approach may have a contraindication to being used when treating ruptured aneurysm, due to the need for additional anti-thrombotic medications. In another procedure, the coils are held in the volume of the aneurysm with a temporary balloon that is inflated in the blood vessel. The balloon is deflated and removed once the mass of coils is secured. In still another procedure, a stent device is placed in the artery to promote flow of blood past the aneurysm. This leads to stagnation of the blood within the aneurysm and thrombosis inside the aneurysm volume. However, a side branch of a main artery in which the stent device is placed may become trapped or "jailed," which can impede access to the side branch. In other instances, the side branch can become clotted off, possibly causing a stroke. Additionally, such a procedure generally requires the use additional anti-thrombotic medications, which limits the use of such devices in the setting of treatment of ruptured aneurysms. The stent device is often formed with a relatively tight weave. While the tight weave increases the effectiveness of the stent device in diverting the blood flow, it also impedes or prevents access to the volume of the aneurysm or the jailed artery. In the event that the aneurysm fails to clot, the obstruction of the aneurysm by the stent device prevents the possibility of placing embolic devices inside the aneurysm. Additional procedures such as the placement of additional stents or open surgery may then be required to treat the residual.

Procedures that involve packing the volume of the aneurysm can suffer from several common shortcomings. First, it can take many coils of wire to fill the volume of the aneurysm, which is time consuming and increases the time it takes to complete the procedure. Further, the coils may be compacted over time to occupy a smaller percentage of the total volume of the aneurysm. A great enough compaction of the coils can be considered a recurrence of the aneurysm and may require further treatment. Aneurysms are often non-spherical in shape and may also or alternatively have mild to severe angulations in relation to the vessel or vessels from which they bulge or protrude. This may make the delivery and employment of one or more aneurysm embolization device to the aneurysm a technical and physical challenge. Systems are presented herein to remedy the difficulties that may occur.

FIG. 1 illustrates an occlusion device 100 configured for placement within an aneurysm. The occlusion device 100 comprises a cover 102 having an outer diameter D. In some embodiments, the cover 102 is circular, with substantially the same diameter D at any transverse measurement around the perimeter. In other embodiments, the cover 102 is non-circular, and may comprise an ellipse, an oval, a polygon or other shapes. In the non-circular embodiments, the cover 102 comprises a minimum transverse dimension and a maximum transverse dimension. In the particular case of an ellipse or an oval shape, the cover 102 comprises a major diameter and a minor diameter. The minor diameter or minimum transverse dimension is configured to be larger than a maximum transverse dimension of an opening into the aneurysm (the neck portion). Thus, the cover 102 is configured to completely cover the neck portion, and thus to cause stagnation of blood within the aneurysm, leading to occlusion. The cover 102 is constructed from a mesh (braided) Nitinol (nickel-titanium alloy) tube 105 that is inverted on itself, thus providing an outer facing surface 108 and an inner facing surface 110. The mesh tube 105 is heat-formed such that cover 102 comprises an expanded portion and a first end 104 and a second end 106 of the tube 105 (FIG. 2) each comprise unexpanded (or partially expanded) portions. A smooth fold 112 extends around the circumference 114 of the cover 102 and represents the transition between the outer facing surface 108 and the inner facing surface 110. The fold 112 avoids any sharp edge that might risk rupture of an aneurysm wall, or other anatomical damage. The cover 102 includes a concavity 116 arranged around a longitudinal axis 118. The cover 102 is fabricated as an inverted mesh tube 105 having a simple straight elongate configuration, and is subsequently formed into the shape shown in FIG. 1, and heat set into this shape. For example, the inverted mesh tube 105 may be constructed as a single layer mesh tube formed of at least some nickel-titanium alloy filaments, and then inverted on itself. The inverted mesh tube 105 may then be placed into a die or mold comprising one or more pieces, to hold it in the shape of the cover 102. Then, the cover 102 may be subjected to an elevated temperature and then cooled, to lock in the shape, resulting in a cover 102 having at least some super-elastic properties.

Figure 3:
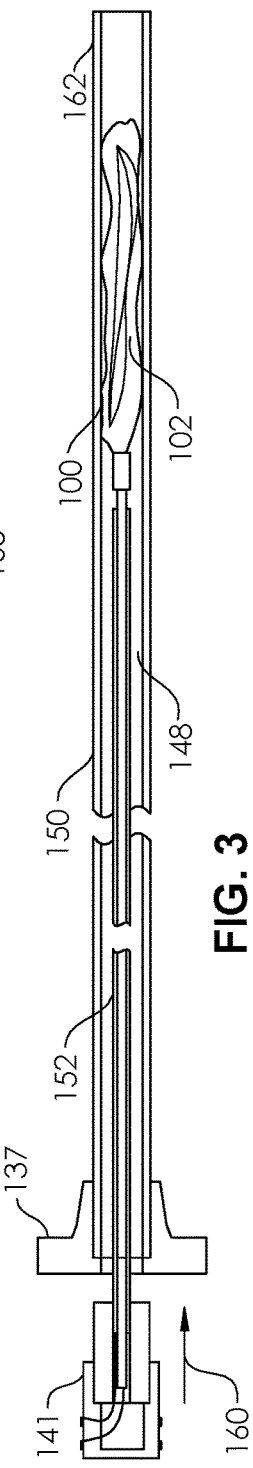
FIG. 3 is a sectional view of the occlusion device of FIG. 2 being delivered within a microcatheter.

As formed (e.g., heat-formed), the cover 102 has an expanded configuration (shown in FIG. 1) and a collapsed configuration, shown in FIG. 3. The cover 102 comprises two mesh layers, provided by the outer facing surface 108 and the inner facing surface 110.

In some embodiments, the cover 102 may comprise some nickel-titanium alloy filaments and some radiopaque elements, comprising platinum, gold, tantalum, or alloys of any of these or other radiopaque materials. In some embodiments, the filaments may comprise drawn filled tubes (DFT), such as those comprising a nickel-titanium alloy outer wall and a platinum core. The radiopaque material allows the cover 102 to be visible on radiographs or fluoroscopy. The occlusion device 100 may be configured by controlling how much radiopaque material is used, by either the ratio of radiopaque filaments to non-radiopaque filaments, or by the amount of platinum core in the drawn filled tubes. In this manner, the cover 102 can be selectively fabricated to be sufficiently visible, but not over visible, e.g., overly bright, such that other objects are obscured. In some embodiments, whether any of the filaments comprise radiopaque materials or not, a marker band 119 may be attached to the proximal end 120 of the occlusion device 100, by adhesive or epoxy bonding, or swaging, welding or other mechanical attachment.

Figure 4:
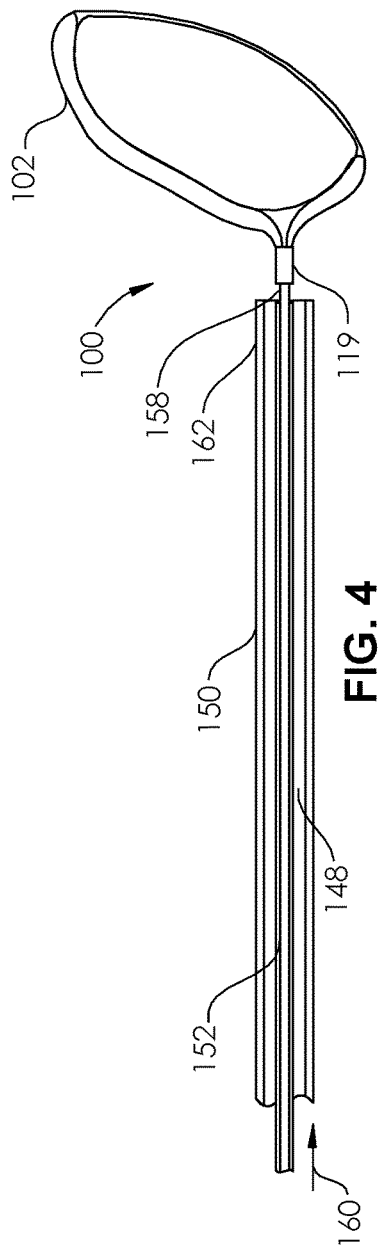
FIG. 4 is a sectional view of the occlusion device of FIG. 2 being deployed from a microcatheter.

A pusher 152, having a distal end 154 and a proximal end 156, may comprise a wire, a hypo tube, or another elongate structure having column support is detachably coupled at its distal end 154 to the proximal end 120 of the occlusion device 100. A detachable joint 158 may comprise one of a number of detachment systems, including but not limited to pressurized detachment, electrolytic detachment mechanisms, hydraulic detachment mechanisms, mechanical or interlocking detachment mechanisms, chemical detachment mechanisms, heat-activated detachment systems, or frictional detachment systems. During delivery, the pusher 152 is held on its proximal end 156 by a user and pushed in a forward longitudinal direction 160 (FIGS. 3-4), in order to advance the occlusion device 100 to the distal end 162 of a delivery catheter 150 (e.g., a microcatheter) having a delivery lumen 148. The delivery catheter 150 may also include a proximal hub 137, such as a luer connector.

Figure 2:
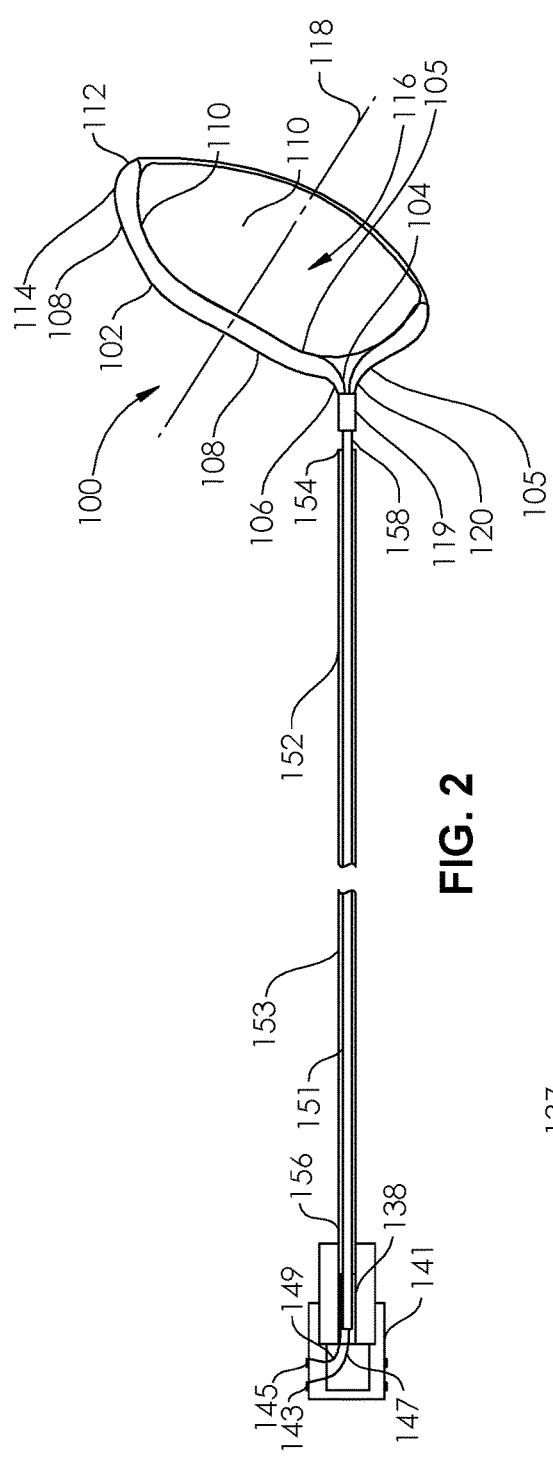
FIG. 2 is a sectional view of the occlusion device according to an embodiment of the present disclosure.

In the embodiment of FIG. 2, the pusher 152 comprises an outer tube 153 and an inner wire 151 coupled to each other. Conductors (e.g., electrical wires) 147, 149 are electrically coupled distally to the inner wire 151 and outer tube 153 (e.g., if a metallic tube), and proximally to first and second circumferential contacts 143, 145 which are carried on a hub 141 that is attached to the proximal end 156 of the pusher 152. The hub 141 has a cavity 138 into which the proximal end 156 of the pusher 152 is inserted and bonded. The hub 141 and its circumferential contacts 143, 145 is reversibly couplable to a connector (not shown) of a detachment controller (not shown), such as those known in the art. The detachment of the occlusion device 100 from the pusher 152 may be achieved by use of the detachment controller by any of the detachment systems, including but not limited to pressurized detachment, electrolytic detachment mechanisms, hydraulic detachment mechanisms, mechanical or interlocking detachment mechanisms, chemical detachment mechanisms, heat-activated detachment systems, or frictional detachment systems.

Figure 5:
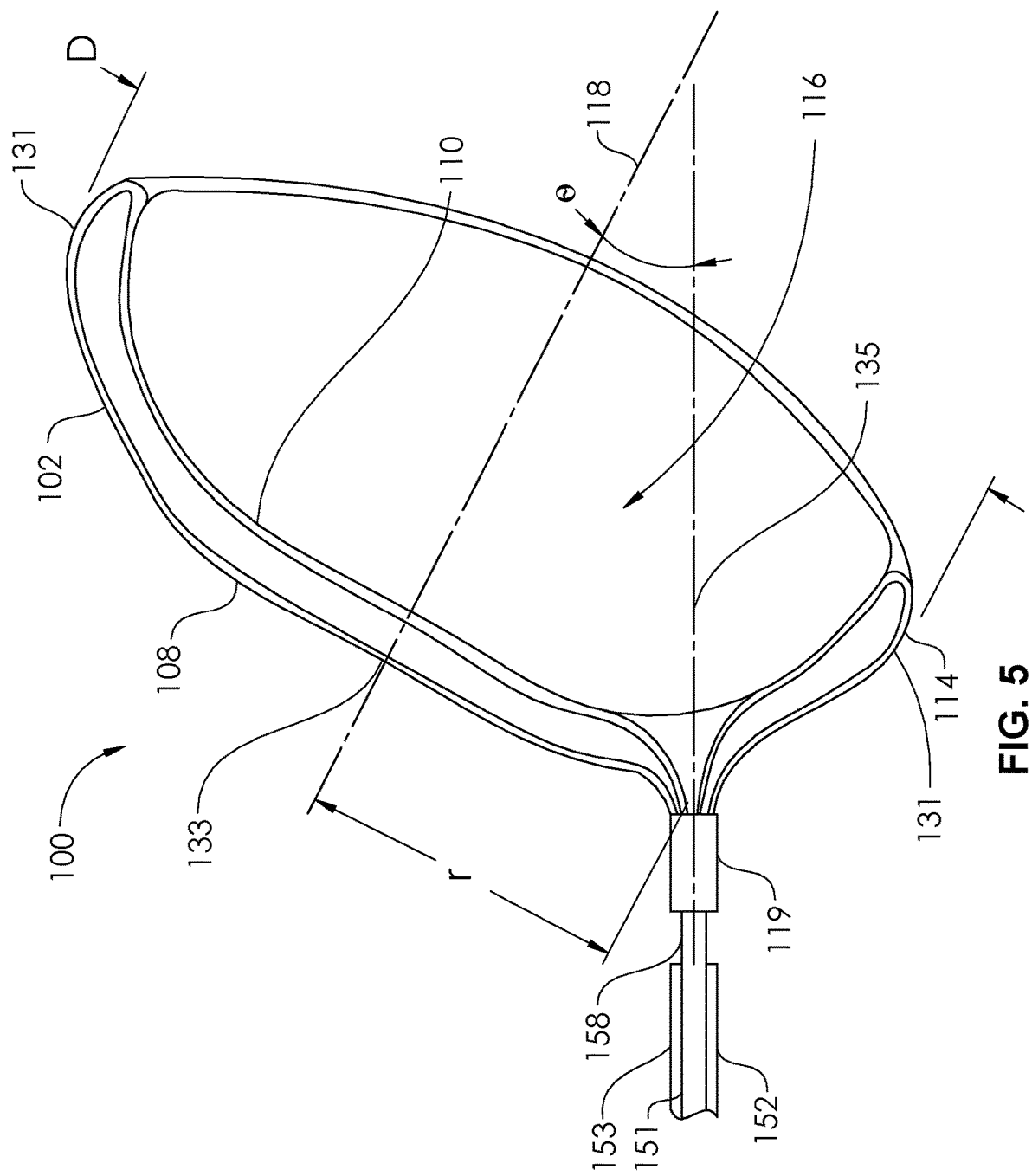
FIG. 5 is a detail sectional view of a distal end of the occlusion device of FIG. 2.

Turning to FIG. 5, the cover 102 of the occlusion device 100 in its expanded configuration includes a concavity 116 arranged generally around a longitudinal axis 118. This does not require that the longitudinal axis 118 be a complete axis of symmetry, as the cover may or may be an elliptical shape, or another non-circular shape. The pusher 152 extends from the detachable joint 158 along its own longitudinal axis 135 that is not colinear with the longitudinal axis 118. A non-zero angle $\theta$ is thus formed between the two longitudinal axes 118, 135. The angle $\theta$ may be between about 15 degrees and about 120 degrees, or between about 30 degrees and about 120 degrees, or between about 40 degrees and about 100 degrees, or between about 45 degrees and about 90 degrees, or between about 75 degrees and about 90 degrees. This angulation aids in the delivery of the occlusion device 100 to an aneurysm that has an angulated takeoff and/or that is located along a tortuous artery or an artery having a severe bend, as will be shown in FIGS. 6A-8C.

Furthermore, the outer facing surface 108 has a general center point 133 at the longitudinal axis 118. The center point 133 (and longitudinal axis 118) are separated from the detachable joint 158 by a non-zero distance r. Thus, the detachable joint 158 is radially offset from the longitudinal axis 118. The maximum radius $r_{MAX}$ of the cover 102 is the largest radius measured from the longitudinal axis 118 to the circumference 131, for example, at any point on the circumference 131 on a generally circular cover, or at a point along the circumference 131 (or in general, perimeter) that is along a major axis, as in an ellipse. The phrase "radially offset," when used herein, should be interpreted as meaning at least about 5% radially offset. In some embodiments, the distance r is at least about 10% of the maximum radius $r_{MAX}$, at least about 25% of the maximum radius $r_{MAX}$, or at least about 50% of the maximum radius, or at least about 75% of the maximum radius $r_{MAX}$. The offset (distance r) aids in the delivery of the occlusion device 100 to an aneurysm that has an angulated takeoff and/or that is located along a tortuous artery or an artery having a severe bend, as will be shown in FIGS. 6A-8C.

Figure 9:
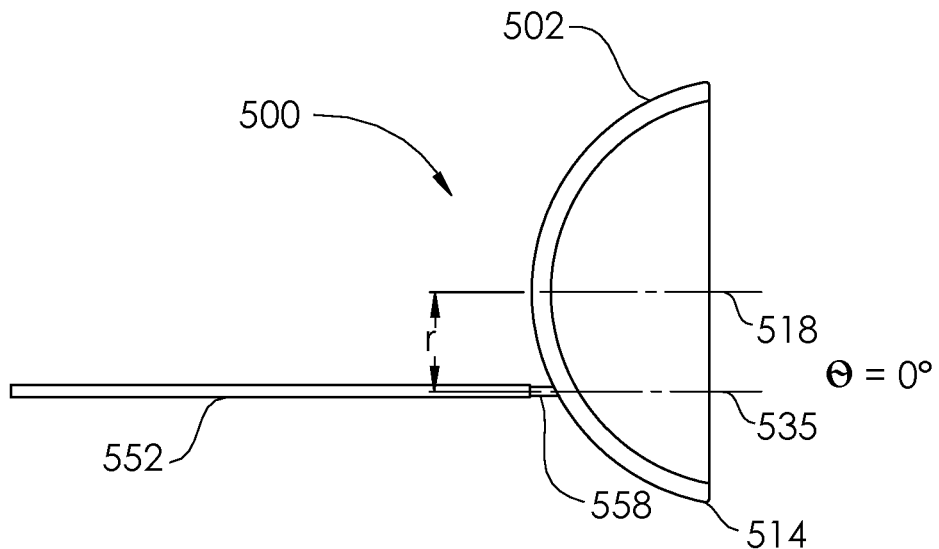
FIG. 9 is a plan view of an occlusion device according to an embodiment of the present disclosure.
Figure 10:
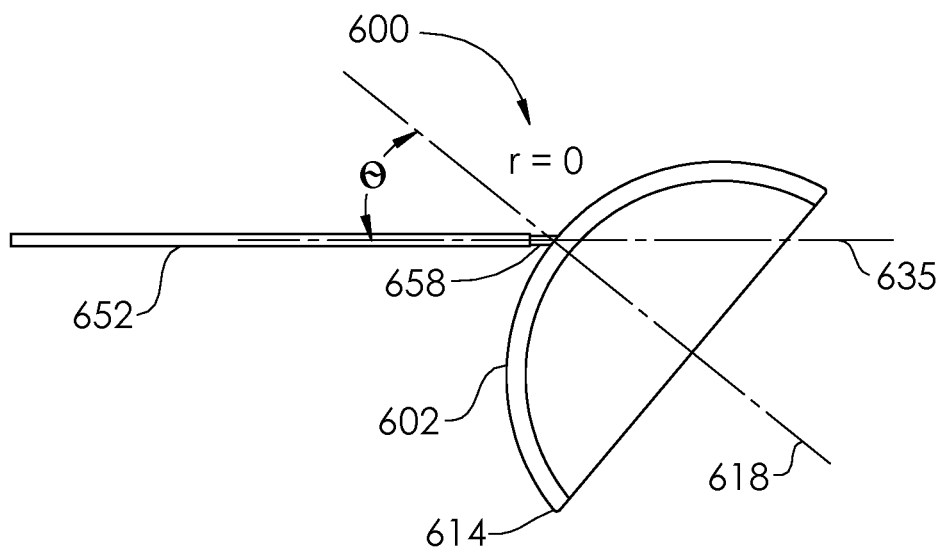
FIG. 10 is a plan view of an occlusion device according to an embodiment of the present disclosure.

Although in FIG. 5 there is both a non-zero angle $\theta$ and a non-zero distance r, in other embodiments, there may be a non-zero angle $\theta$ but a substantially zero distance r, as in the occlusion device 600 of FIG. 10. In other embodiments, there may be a non-zero distance r and a substantially zero degree angle $\theta$, as in the occlusion device 500 of FIG. 9.

FIGS. 6A-8C illustrate arteries 702, 802, 902 having sidewall aneurysms 700, 800, 900. The approach by catheter (e.g., delivery catheter/microcatheter 150) in a sidewall aneurysm is often challenging when placing a single occlusion device. A distal end 162 of the delivery catheter 150 may be supplied preshaped with a particular curve, or may be steam shaped or shaped by other manners by a user, to create a preferred curve, prior to the insertion of the delivery catheter 150 into the patient's vasculature, such that the delivery angle of occlusion devices 200, 300, 400 into the aneurysm 700, 800, 900 allows a delivery along an axis that is substantially or somewhat parallel to a longitudinal axis of the neck 706, 806, 906 of the aneurysm 700, 800, 900, or substantially or somewhat parallel to a longitudinal axis of the sac of the aneurysm 700, 800, 900 itself. However, the curvature of the artery 702, 802, 902 or a small diameter of the artery 702, 802, 902 may make it difficult for a curved tip of a delivery catheter 150 to fit in the artery 702, 802, 902, adjacent the neck 706, 806, 906. In other cases, the curved tip may not be able to provide sufficient backup support for delivering the implant (occlusion device). Occlusion devices 200, 300, 400 according to the embodiments disclosed herein ameliorate the efficacy of embolizations performed in these anatomical conditions by allowing the user to choose particular device parameters that match the anatomy.

In FIG. 6A an occlusion device 200 comprising a cover 202 detachably coupled to a pusher 252 at a detachable joint 258 is delivered through a delivery catheter 150 to an aneurysm 700 extending from an artery 702. The aneurysm 700 includes a dome 704 and a neck 706. The occlusion device 200 is similar to the occlusion device 100, but has a different angle $\theta$ and offset distance r, as seen in FIG. 6A. The particular occlusion device 200 (e.g., size, specification, model) may be chosen by the attending physician to fit the aneurysm 700, with the angle $\theta$ and offset distance r particularly chosen to aid the delivery through the artery 702 and into the aneurysm 700, and to optimize the geometry of the system (e.g. delivery catheter 150 and occlusion device 200) during detachment. The cover 202 has a concavity 216 and an outer perimeter 214, or circumference (FIG. 6C). In FIG. 6B, the cover 202 is detached from the pusher 252 via the detachable joint 258 in any one of the manners described in relation to the occlusion device 100. The pusher 252 and the delivery catheter 150 are then removed from the patient, leaving the occlusion device 200 deployed within the aneurysm 700, as shown in FIG. 6C. The outer facing surface 208 of the cover 202 is seated against a lower wall portion 708 of the aneurysm 700 sac, against the neck 706 of the aneurysm 700. The outer perimeter 214 extends into the sac, at least at some of its portions, and extends in a direction substantially away from the neck 706 of the aneurysm 700.

In FIG. 7A an occlusion device 300 comprising a cover 302 detachably coupled to a pusher 352 at a detachable joint 358 is delivered through a delivery catheter 150 to an aneurysm 800 extending from an artery 802. The aneurysm 800 includes a dome 804 and a neck 806. The occlusion device 300 is similar to the occlusion device 100, but has a different angle θ and offset distance r, as seen in FIG. 7A. The particular occlusion device 300 (e.g., size, specification, model) may be chosen by the attending physician to fit the aneurysm 800, with the angle θ and offset distance r particularly chosen to aid the delivery through the artery 802 and into the aneurysm 800, and to optimize the geometry of the system (e.g. delivery catheter 150 and occlusion device 300) during detachment. The cover 302 has a concavity 316 and an outer perimeter 314, or circumference (FIG. 7C). In FIG. 7B, the cover 302 is detached from the pusher 352 via the detachable joint 358 in any one of the manners described in relation to the occlusion device 100. The pusher 352 and the delivery catheter 150 are then removed from the patient, leaving the occlusion device 300 deployed within the aneurysm 800, as shown in FIG. 7C. The outer facing surface 308 of the cover 302 is seated against a lower wall portion 808 of the aneurysm 800 sac, against the neck 806 of the aneurysm 800. The outer perimeter 314 extends into the sac, at least at some of its portions, and extends in a direction substantially away from the neck 806 of the aneurysm 800.

In FIG. 8A an occlusion device 400 comprising a cover 402 detachably coupled to a pusher 452 at a detachable joint 458 is delivered through a delivery catheter 150 to an aneurysm 900 extending from an artery 902. The aneurysm 900 includes a dome 904 and a neck 906. The occlusion device 400 is similar to the occlusion device 100, but has a different angle θ and offset distance r, as seen in FIG. 8A. The particular occlusion device 400 (e.g., size, specification, model) may be chosen by the attending physician to fit the aneurysm 900, with the angle θ and offset distance r particularly chosen to aid the delivery through the artery 902 and into the aneurysm 900, and to optimize the geometry of the system (e.g. delivery catheter 150 and occlusion device 400) during detachment. The cover 402 has a concavity 416 and an outer perimeter 414, or circumference (FIG. 8C). In FIG. 8B, the cover 402 is detached from the pusher 452 via the detachable joint 458 in any one of the manners described in relation to the occlusion device 100. The pusher 452 and the delivery catheter 150 are then removed from the patient, leaving the occlusion device 400 deployed within the aneurysm 900, as shown in FIG. 8C. The outer facing surface 408 of the cover 402 is seated against a lower wall portion 908 of the aneurysm 900 sac, against the neck 906 of the aneurysm 900. The outer perimeter 414 extends into the sac, at least at some of its portions, and extends in a direction substantially away from the neck 906 of the aneurysm 900.

Figure 6:
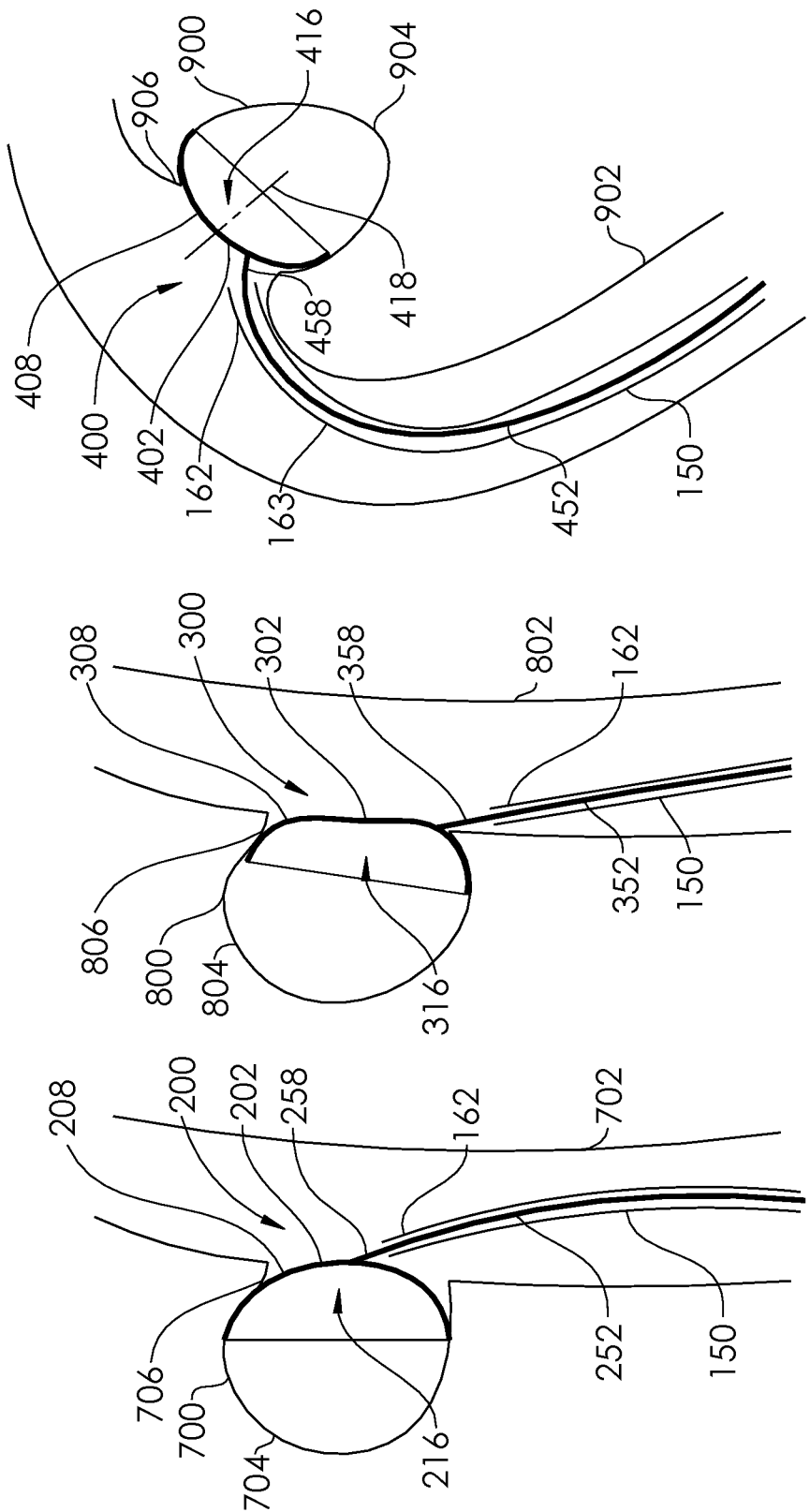
FIGS. 6A-6C are sectional views of the delivery of an occlusion device of an occlusion system into an aneurysm according to an embodiment of the present disclosure.
Figure 7:
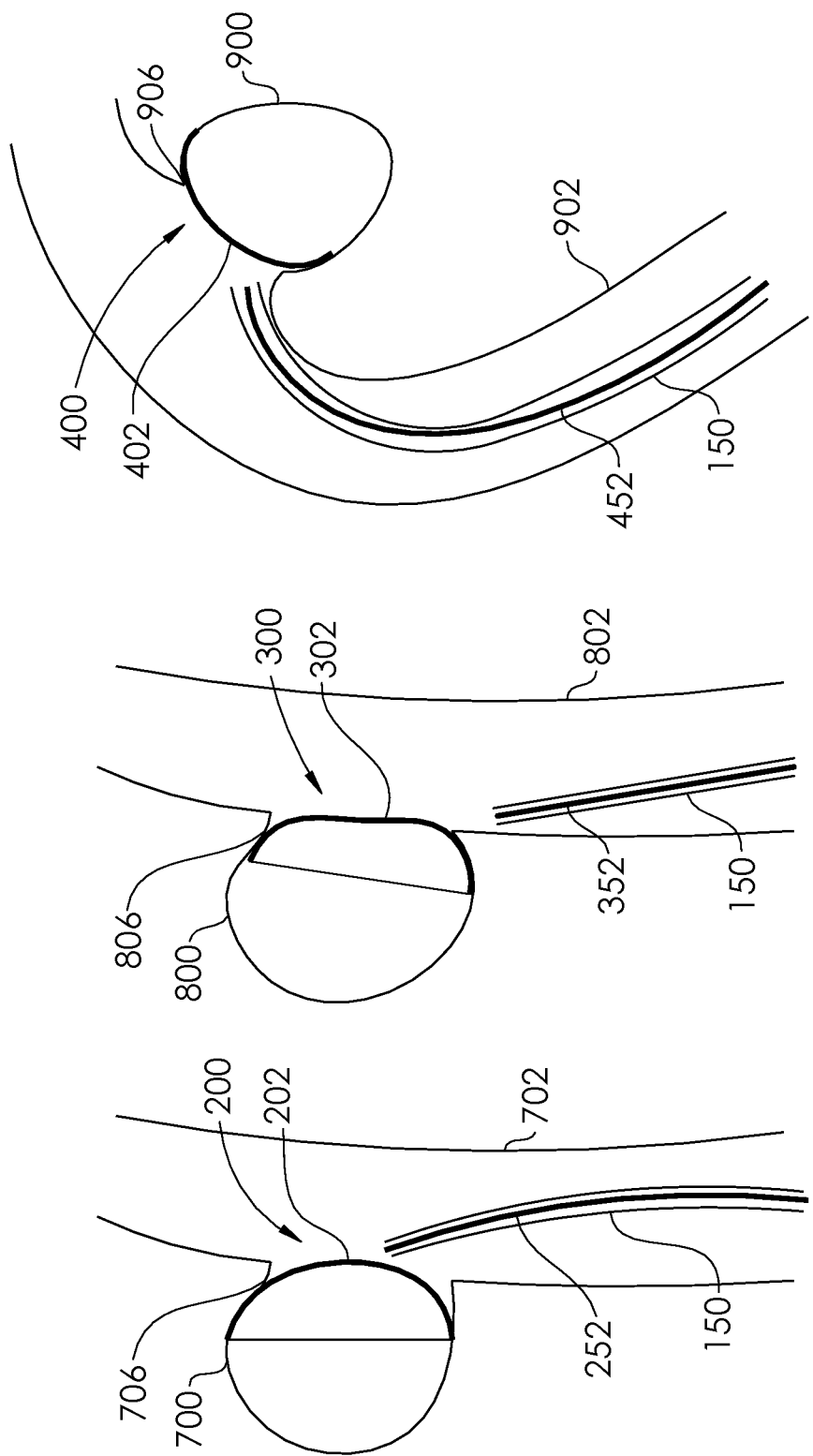
FIGS. 7A-7C are sectional views of the delivery of an occlusion device of an occlusion system into an aneurysm according to an embodiment of the present disclosure.
Figure 8:
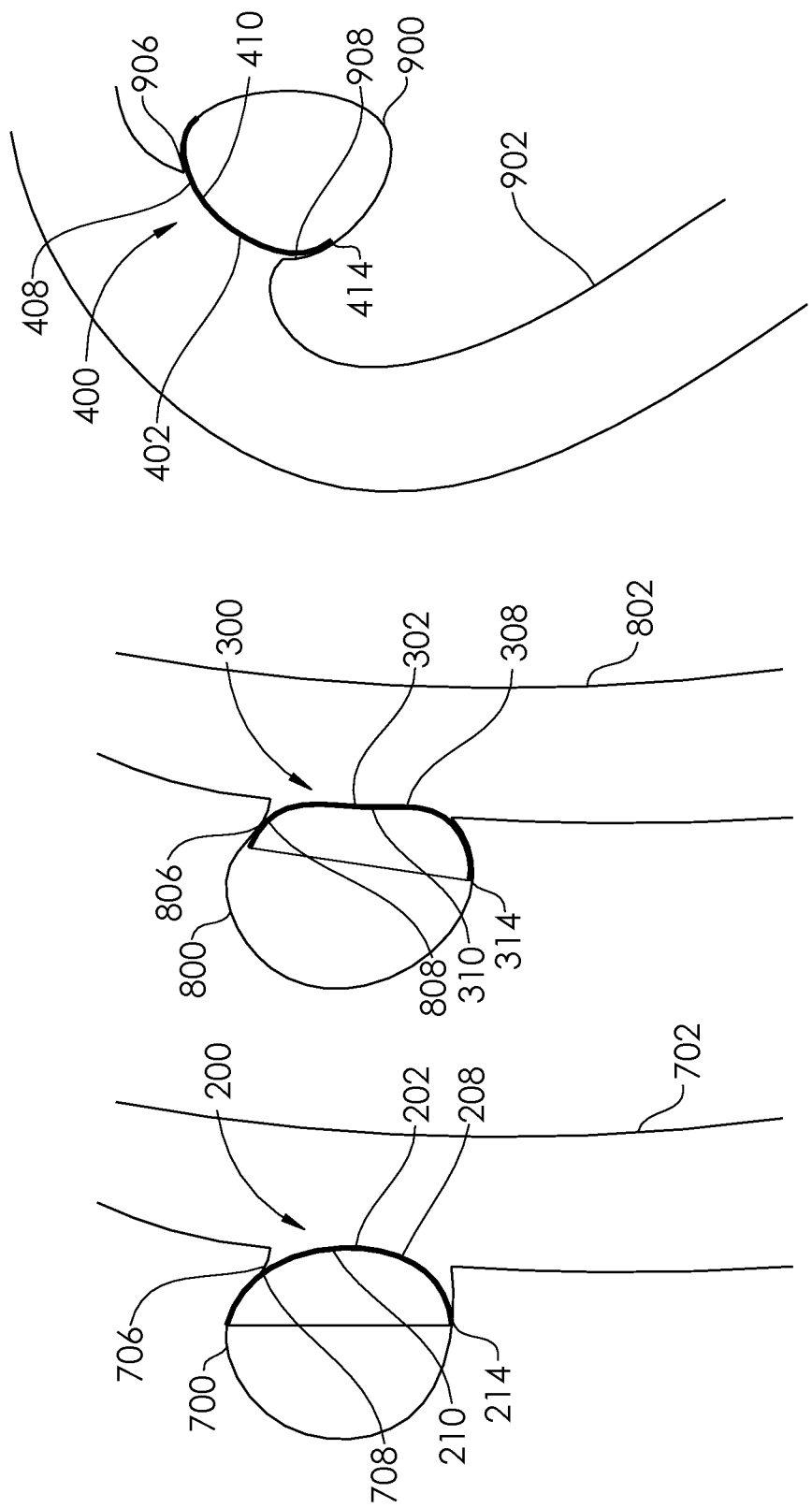
FIGS. 8A-8C are sectional views of the delivery of an occlusion device of an occlusion system into an aneurysm according to an embodiment of the present disclosure.

As can be seen in FIGS. 6A-8C, the particular angle θ and/or offset distance r make possible optimized delivery and deployment of the occlusion devices 200, 300, 400 within the aneurysms 700, 800, 900. In FIGS. 6A and 7A, the delivery catheter 150 is shown having little or no curve formed onto its distal end 162. However, in FIG. 8A, the distal end 162 has a curve 163 preformed or physician-formed, to aid the delivery of the occlusion device 400 into the aneurysm 900. The curve 163 is more or less oriented along the plane of the page, with radius or radii or curvature that are substantially orthogonal to the page (i.e., extend vertically from the page). However, because the occlusion device 400 has a concave shape arrange around a longitudinal axis 418, and because the occlusion device 400 and pusher 452 together form a structure that is asymmetric to the longitudinal axis 418, it may be desirable to selectively control the oriental rotation of the occlusion device 400 in relation to its longitudinal axis 418, which would thus further control the overall orientation of the occlusion device 400 in relation to the aneurysm 900.

Returning to FIG. 1, the cover 102 may be braided such that the braiding, mesh, etc., is arranged somewhat symmetrically around the longitudinal axis 118. However, it may also be desired in alternative embodiments to asymmetrically form the braiding around the longitudinal axis 118, such that when the cover 102 is compressed into its collapsed configuration, it actually preferentially favors (via structure and sliding mechanics) forming a more linear structure, oriented more along the longitudinal axis 135 (FIG. 5). Thus, while compressed within the lumen 148 of the delivery catheter 150, the longitudinal axis 118 and the "pseudo" longitudinal axis 135 (because the cover 102 is now temporarily deformed) are now forced into an angle θ of substantially 90 degrees (in relation to each other). That is, until the cover 102 is delivered from the lumen 148 of the delivery catheter 150, allowing it to take its expanded configuration, and, via the memory of the braid material, to conform to its true angle θ. The asymmetric braiding may be achieved by using a braiding process or automated braiding machine that varies the braid angle in an oscillating or sinusoidal manner. For example, at a particular clock location around the circumference 114 of the cover 102 (e.g., 6 o'clock) the braid angle may equal a first value X and at another clock location around the circumference 114 of the cover 102 (e.g., 9 o'clock) the braid angle may equal a second value 0.8X. In some embodiments, the second value may be between about 40% and about 95% of the first value, or between about 50% and about 90% of the first value, or between about 60% and about 85% of the first value.

FIG. 9 illustrates an occlusion device 500 comprising a cover 502 detachably coupled to a pusher 552 at a detachable joint 558. The cover 502 has an outer perimeter 514. The longitudinal axis 518 of the cover 502 is radially offset from the longitudinal axis 535 of the pusher 552 by a non-zero distance r. There is substantially a zero angle between the longitudinal axis 518 of the cover and the longitudinal axis 535 of the pusher 552.

FIG. 10 illustrates an occlusion device 600 comprising a cover 602 detachably coupled to a pusher 652 at a detachable joint 658. The cover 602 has an outer perimeter 614. The longitudinal axis 618 of the cover 602 is angled from the longitudinal axis 635 of the pusher 652 by a non-zero angle θ. There is substantially a zero distance r between the longitudinal axis 618 of the cover and the longitudinal axis 635 of the pusher 652.

Though the occlusion devices 100, 200, 300, 400, 500, 600 as described according to embodiments disclosed herein are shown generally having a proximal convexity and a distal concavity, and are configured to predominantly being placed in a lower (near the neck) portion of an aneurysm, any other configuration for an aneurysm occlusion device is also contemplated for use in combination with the attachment/detachment geometries taught in the embodiments disclosed. This includes devices configured to be the only device implanted in the aneurysm, as well as devices configured to be one or a plurality of devices implanted in the aneurysm. FIGS. 11-16 illustrate six different occlusion systems 770, 772, 774, 776, 778, 780 being utilized to deliver a braided shell 758 into an aneurysm 750 having a dome 752 and a neck 768. The braided shell 758 has a longitudinal axis 756 and is configured to fill a majority of the aneurysm 750 or in some cases substantially all of the aneurysm 750 sac. The braided shell 758 is braided or woven from filaments 760, and has a proximal end 751, a distal end 753, and an intermediate portion 782. The aneurysm 750 has the geometry of a sidewall aneurysm in relation to left extending artery 762 and right extending artery 764. The aneurysm 750 alternatively has the geometry of a terminal aneurysm in relation to artery 754. An additional vessel 766 may also be present. It may be desired to avoid the embolization of this vessel 766 in the process of embolizing the aneurysm 750.

Figure 11:
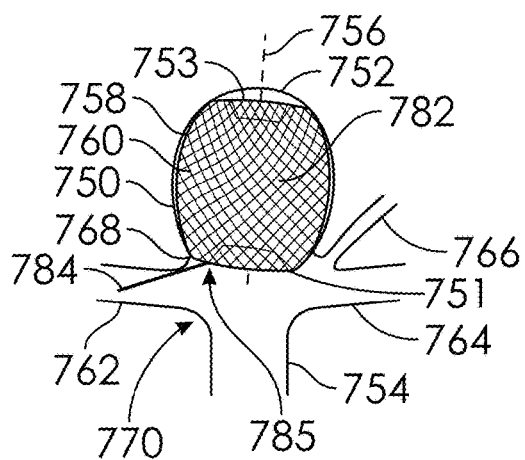
FIG. 11 is a perspective view of the delivery of an occlusion device of an occlusion system into an aneurysm according to an embodiment of the present disclosure.

In FIG. 11, the occlusion system 770 includes a pusher 784 that is detachably coupled to the proximal end 751 of the braided shell 758 at a detachable joint 785. The pusher 784 extends from the detachable joint 785 at a non-zero angle in relation to the longitudinal axis 756 of the braided shell 758. The detachable joint 785 is dimensionally offset a non-zero distance from the longitudinal axis 756 of the braided shell 758. The offset side is the same as the side that the pusher 784 extends. The occlusion system 770 is shown in FIG. 11 being delivered from the artery 762, though it may also be delivered from one or more other arteries.

Figure 12:
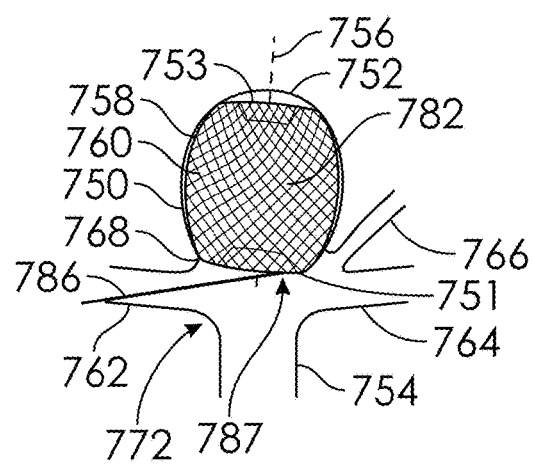
FIG. 12 is a perspective view of the delivery of an occlusion device of an occlusion system into an aneurysm according to an embodiment of the present disclosure.

In FIG. 12, the occlusion system 772 includes a pusher 786 that is detachably coupled to the proximal end 751 of the braided shell 758 at a detachable joint 787. The pusher 786 extends from the detachable joint 787 at a non-zero angle in relation to the longitudinal axis 756 of the braided shell 758. The detachable joint 787 is dimensionally offset a non-zero distance from the longitudinal axis 756 of the braided shell 758, which is located on an opposite side of the longitudinal axis from the side that the pusher 784 extends. The occlusion system 772 is shown in FIG. 12 being delivered from the artery 762, though it may also be delivered from one or more other arteries.

Figure 13:
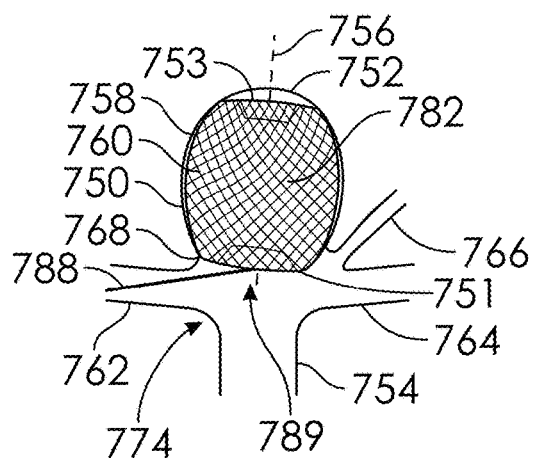
FIG. 13 is a perspective view of the delivery of an occlusion device of an occlusion system into an aneurysm according to an embodiment of the present disclosure.

In FIG. 13, the occlusion system 774 includes a pusher 788 that is detachably coupled to the proximal end 751 of the braided shell 758 at a detachable joint 789. The pusher 788 extends from the detachable joint 789 at a non-zero angle in relation to the longitudinal axis 756 of the braided shell 758. The detachable joint 789 is generally not offset from the longitudinal axis 756 of the braided shell 758, but is instead coupled substantially at the longitudinal axis 756. The occlusion system 774 is shown in FIG. 13 being delivered from the artery 762, though it may also be delivered from one or more other arteries.

Figure 14:
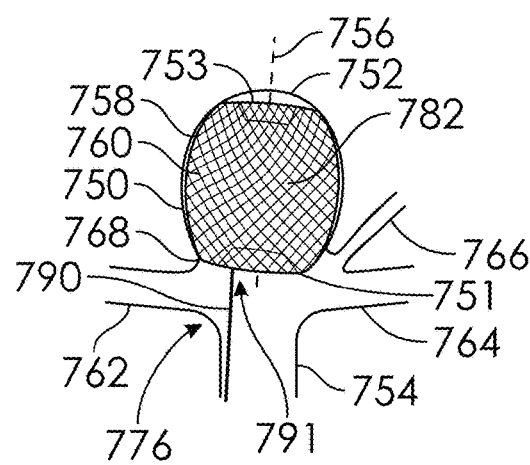
FIG. 14 is a perspective view of the delivery of an occlusion device of an occlusion system into an aneurysm according to an embodiment of the present disclosure.

In FIG. 14, the occlusion system 776 includes a pusher 790 that is detachably coupled to the proximal end 751 of the braided shell 758 at a detachable joint 791. The pusher 790 extends from the detachable joint 791 at a substantially zero angle in relation to the longitudinal axis 756 of the braided shell 758. The detachable joint 791 is dimensionally offset a non-zero distance from the longitudinal axis 756 of the braided shell 758. The occlusion system 776 is shown in FIG. 14 being delivered from the artery 754, though it may also be delivered from one or more other arteries.

Figure 15:
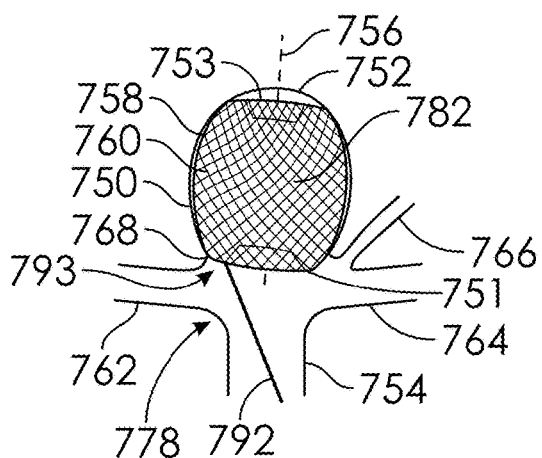
FIG. 15 is a perspective view of the delivery of an occlusion device of an occlusion system into an aneurysm according to an embodiment of the present disclosure.

In FIG. 15, the occlusion system 778 includes a pusher 792 that is detachably coupled to the proximal end 751 of the braided shell 758 at a detachable joint 793. The pusher 792 extends from the detachable joint 793 at a non-zero angle in relation to the longitudinal axis 756 of the braided shell 758. The detachable joint 793 is dimensionally offset a non-zero distance from the longitudinal axis 756 of the braided shell 758. The offset side is opposite of the side that the pusher 792 extends. The occlusion system 778 is shown in FIG. 15 being delivered from the artery 754, though it may also be delivered from one or more other arteries.

Figure 16:
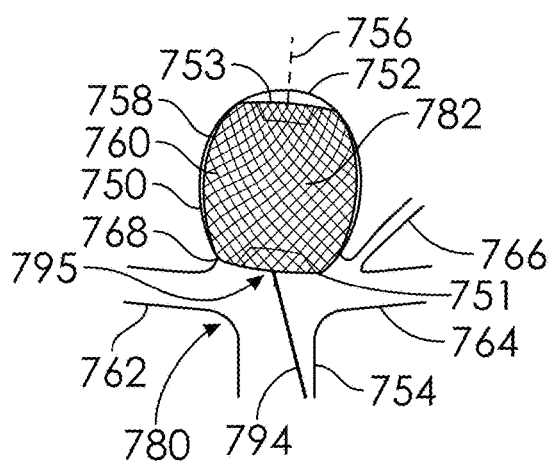
FIG. 16 is a perspective view of the delivery of an occlusion device of an occlusion system into an aneurysm according to an embodiment of the present disclosure.

In FIG. 16, the occlusion system 780 includes a pusher 794 that is detachably coupled to the proximal end 751 of the braided shell 758 at a detachable joint 795. The pusher 794 extends from the detachable joint 795 at a non-zero angle in relation to the longitudinal axis 756 of the braided shell 758. The detachable joint 795 is not offset from the longitudinal axis 756 of the braided shell 758, but is instead coupled substantially at the longitudinal axis 756. The occlusion system 780 is shown in FIG. 16 being delivered from the artery 754, though it may also be delivered from one or more other arteries.

As can be seen in FIGS. 11-16, the angle θ and/or offset distance r make possible optimized delivery and deployment of the occlusion devices (braided shell 758) within the aneurysm 750.

Figure 17:
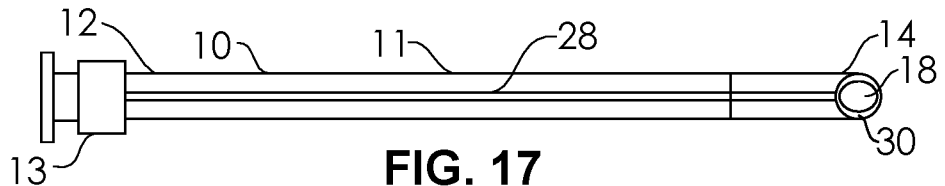
FIG. 17 is a top view of a delivery catheter according to an embodiment of the present disclosure.
Figure 18:
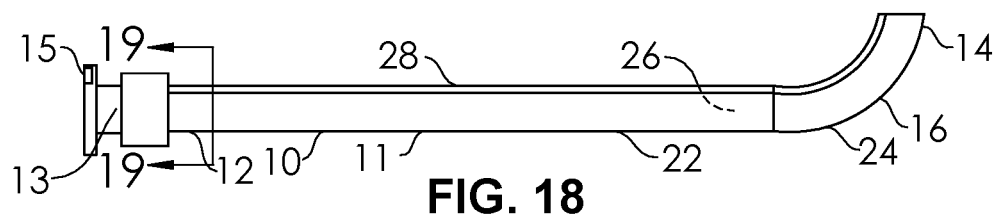
FIG. 18 is a side view of the delivery catheter of FIG. 17.
Figure 19:
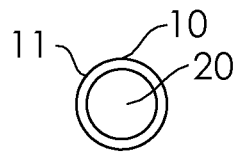
FIG. 19 is a magnified cross-section view taken along line 19 of FIG. 18.

FIGS. 17 and 18 illustrate a delivery catheter 10 comprising a shaft 11 having a proximal end 12, a distal end 14 having a curve 16, and a non-circular lumen 18. A luer hub 13 is bonded to the proximal end 12 of the shaft 11. In some embodiments, the non-circular lumen 18 may extend through the entirety of the shaft 11, but in the embodiment of FIGS. 17 and 18, the non-circular lumen 18 morphs into a circular lumen 20 (FIG. 19) at the proximal end 12. In some embodiments, the shaft 11 may be extruded with a circular lumen 20 its entire length, and then a non-circular cross-section mandrel may be placed in the lumen 20 at the distal end 14, and heat may be applied to reform the lumen 20 at the distal end 14 to have the non-circular lumen 18 shape. In other embodiments, a first tubular portion 22 having a circular lumen 20 may be thermally fused to a second tubular portion 24 having a non-circular lumen 18. The mandrel may be placed from the proximal end, and have smooth transitions between a circular outer cross-section and a non-circular outer cross-section, in order to form a transition zone 26 comprising a continuously smooth luminal wall surface transition between the circular lumen 20 and the non-circular lumen 18. The non-circular lumen 18 is illustrated in FIG. 17 as an ellipse, buy may alternately by an oval, or any type of non-circular cross-sectional shape. For example, a polygonal shape, a dogbone shape, a guitar shape, or a U-shape. Optionally, to further aid visualization on fluoroscopy (e.g., biplane fluoroscopy), a radiopaque stripe 28 may be extruded or otherwise placed on one side of the wall 30 of the shaft 11. Thus, a physician delivering the delivery catheter 10 is able to better judge the orientation (the clock position of rotation) of the curve 16 in relation to an aneurysm. The non-circular lumen 18 allows an occlusion device whose compressed or constrained profile is substantially oval or elliptical, or otherwise non-circular, to be selectively oriented rotationally, for example, such that it can only be placed at 0°, or placed at 180°, or at another angle of rotation. A marking 15 on the luer hub 13 can be used to aid the insertion of the occlusion device such that it is oriented at a particular one of the 0° or 180° orientation, by serving as a comparative visual aid. In some embodiments, longitudinal stripes may be placed on the shaft 11 near the distal end 14, to allow steam shaping of the curve 16 (if not preshaped), or reshaping of the curve 16, along a desired plane. In some embodiments, steam shaping can be done by placing a bendable mandrel within the non-circular lumen 18 to further or alternatively aid the shaping or reshaping of the curve 16 along a desired plane. In some embodiments, the bendable mandrel has a similar cross-section shape as the non-circular lumen 18, such that it substantially fills the non-circular lumen 18.

Figure 20:
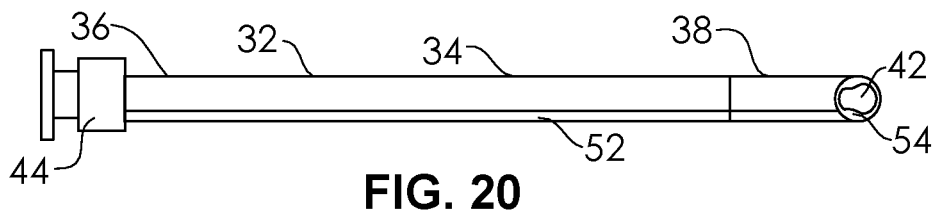
FIG. 20 is a top view of a delivery catheter according to an embodiment of the present disclosure.
Figure 21:
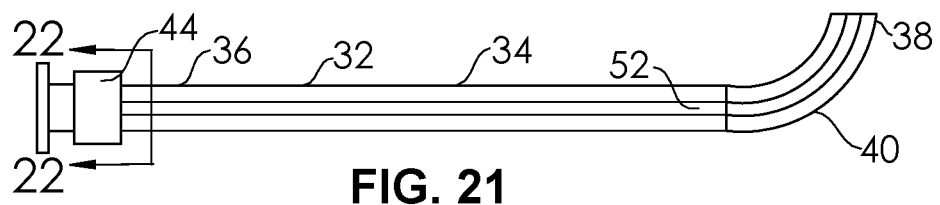
FIG. 21 is a side view of the delivery catheter of FIG. 20.
Figure 22:
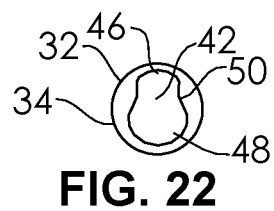
FIG. 22 is a magnified cross-section view taken along line 22 of FIG. 21.

FIGS. 20 and 21 illustrate a delivery catheter 32 comprising a shaft 34 having a proximal end 36, a distal end 38 having a curve 40, and a non-circular lumen 42. A luer hub 44 is bonded to the proximal end 36 of the shaft 34. In this particular embodiment, the non-circular lumen 42 extends through the entirety of the shaft 34. The non-circular lumen 42 is illustrated in FIG. 20 as a guitar shape having a first, smaller lobe 46 and a second, larger lobe 48 that are joined together by a waist 50. The guitar shape thus creates a key for allowing only one particular rotational positional of the occlusion device when it exits from the lumen 42 at the distal end 38 of the shaft 34, and thus, into the aneurysm. In some embodiments, the non-circular lumen 42 may taper down in size near the distal end 38 of the shaft 34. Thus, the occlusion device is held substantially tightly near the distal end 38 of the shaft 34, but there is more space through most of the length of the lumen 42, to minimize axial friction. Any other type of "keyed" shape may alternatively be used for the non-circular lumen 42. Optionally, to further aid visualization on fluoroscopy (e.g., biplane fluoroscopy), a longitudinal radiopaque stripe 52 may be extruded or otherwise placed on one side of the wall 54 of the shaft 34.

Turning to FIGS. 23-26, a loading sheath (or introducer sheath or insertion sheath) 56 is configured to aid in the insertion of an asymmetric occlusion device 58 (or asymmetric occlusion device 58/pusher 59/detachable joint 61 system) into the non-circular lumen 60 (FIG. 26) of a delivery catheter 62. The non-circular lumen 60 may only extend within the shaft 64 of the catheter 62, or the luer hub 66 itself may also have the non-circular lumen 60 (as illustrated in FIG. 26). A removable funnel 68 has a proximal end 70 attached to a distal end 72 of the loading sheath 56. The funnel 68 has a proximal inner diameter 74 (FIG. 25) that matches the diameter 76 at the distal end 72 of the loading sheath 56. The funnel 68 smoothly tapers up to an increased inner diameter 78 at a distal end 80. In use, the occlusion device 58 may be packaged inside the lumen 82 of the loading sheath 56 or may be packaged extending from the loading sheath 56. Prior to insertion into the non-circular lumen 60 of the delivery catheter 62, the occlusion device 58 may be prepared by priming or flushing the lumen 82 (FIG. 23) of the loading sheath 56. The occlusion device 58 may be examined or rinsed in saline or in saline and heparin, external to the loading sheath 56, as shown in FIG. 23. The user then carefully applies traction on (pulls) the pusher 59 to load the occlusion device 58 into the lumen 82 of the loading sheath 56 in the preferred compressed configuration. For example, with folded portions oriented in the most low-profile manner, or with the preferred distally extending portions configured such that they will exit the lumen 82 first. The inner contours of the funnel 68 optimize the ability to preferentially load the occlusion device 58 into the lumen 82. For example, the preferential loading may be done in a manner to obtain the smallest possible compressed or collapsed diameter. The loaded occlusion device 58 is shown in FIG. 24, fully within the lumen 82 of the loading sheath 56. As shown in FIG. 25, the funnel 68 can then be snapped off, unscrewed from, or otherwise removed from the loading sheath 56. The funnel 68 can then be removed and discarded. In some embodiments, the funnel 68 may be reattachable to the loading sheath 56 Turning to FIG. 26, the distal end 72 of the loading sheath 56 is placed close to the entrance of the non-circular lumen 60 such that, for example, a larger profile lobe 84 of the compressed occlusion device 58 can be matched for entry into the larger lobe 86 of the non-circular lumen 60, and a smaller profile lobe 88 of the occlusion device 58 can be matched for entry into the smaller lobe 90 of the non-circular lumen 60. The pusher 59 is then pushed by the user to load the occlusion device 58 in the non-circular lumen 60, and to advance the occlusion device 58 toward the distal end (not shown) of the delivery catheter 62. The loading sheath 56 may be peel-away, or may simply be pulled back to a proximal portion of the pusher 59. The occlusion device 58 can now be reliably delivered to an aneurysm in the chosen orientation. For example, correct-side-up, instead of upside-down. In some embodiments, the loading sheath may have external longitudinal stripes on the tubing to aid the user in applying the desired rotational orientation when inserting the occlusion device 58.

Alternative luminal shapes and occlusion device compressed shapes are shown in FIGS. 27A-27E. In the embodiment of FIG. 27A, the distal end 852 of a delivery catheter 850 has a non-circular lumen 854 having a pentagonal shape. An occlusion device 856 in its compressed configuration favors a substantially pentagonal shape that is keyable to the shape of the non-circular lumen 854. In the embodiment of FIG. 27B, the distal end 858 of a delivery catheter 860 has a non-circular lumen 862 having a diamond shape. An occlusion device 864 in its compressed configuration favors a substantially diamond shape that is keyable to the shape of the non-circular lumen 862. In the embodiment of FIG. 27C, the distal end 866 of a delivery catheter 868 has a non-circular lumen 870 having a U-shape. An occlusion device 872 in its compressed configuration favors a substantially U-shape that is keyable to the shape of the non-circular lumen 870. In the embodiment of FIG. 27D, the distal end 874 of a delivery catheter 876 has a non-circular lumen 878 having an oval shape. An occlusion device 880 in its compressed configuration favors a substantially oval shape that is keyable to the shape of the non-circular lumen 878. In the embodiment of FIG. 27E, the distal end 882 of a delivery catheter 884 has a non-circular lumen 886 having a guitar shape. An occlusion device 888 in its compressed configuration favors a substantially guitar shape that is keyable to the shape of the non-circular lumen 886.

Figure 28:
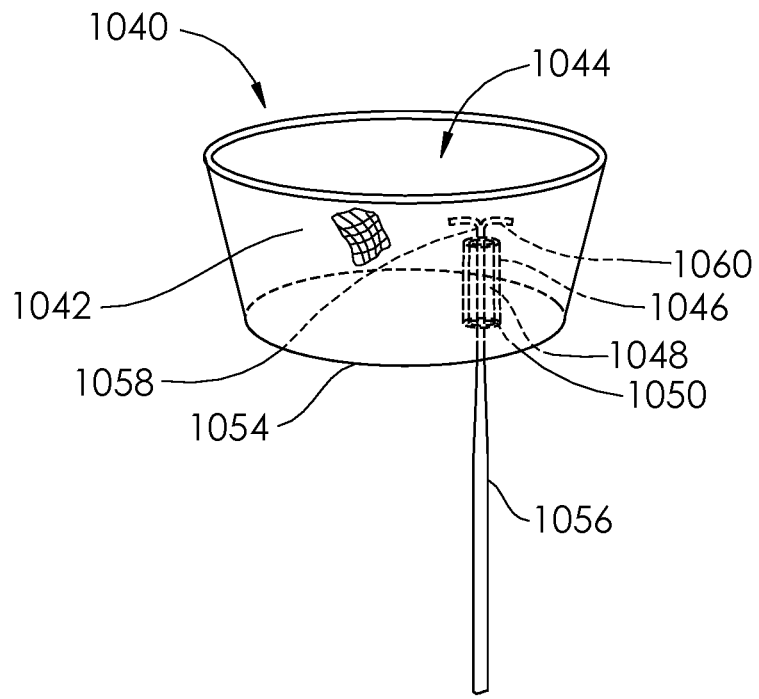
FIG. 28 is a perspective view of an occlusion device according to an embodiment of the present disclosure.
Figures 29A, 29B, 29C:
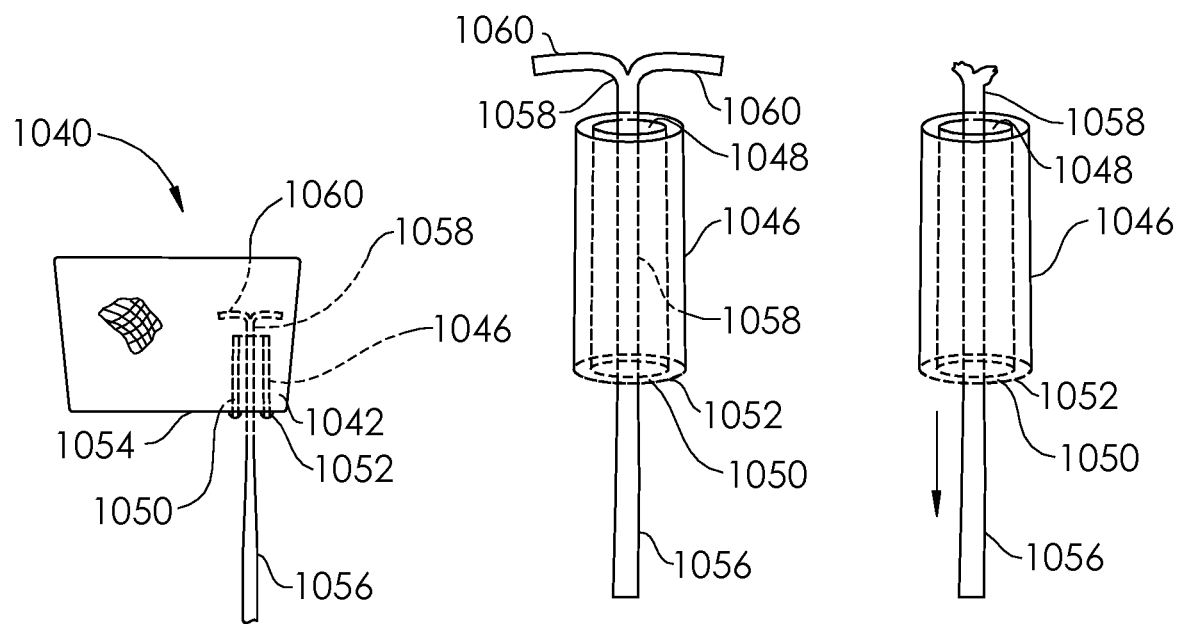
FIG. 29A is a side view of the occlusion device of FIG. 28.
FIG. 29B is a detail view of the detachment portion of the occlusion device of FIG. 28, prior to detachment.
FIG. 29C is a detail view of the detachment portion of the occlusion device of FIG. 28, during detachment.

FIGS. 28-29C illustrate an occlusion device 1040 comprising a mesh cover 1042 including a distal concavity 1044. A radially offset internal tube 1046 having a lumen 1048 and an outer wall 1050 is secured within the mesh cover 1042, such that its proximal end 1052 is flush or closely adjacent to a proximal end 1054 of the mesh cover 1042. A pusher 1056 comprises a wire having a distal end 1058 including a plurality of radially-extending fingers 1060 which extend from the distal end 1058. The fingers 1060 are configured to be meltable, detachable, unbendable, breakable, ablatable, deformable, or otherwise changeable. Prior to detachment, the radially-extending fingers 1060 create a maximum diameter that is larger than the diameter of the lumen 1048 of the internal tube 1046, such that traction on the wire of the pusher 1056 causes the fingers 1060 to pull on the distal end of the outer wall 1050 of the internal tube 1046, and thus the pull the entire occlusion device 1040. For example, the occlusion device 1040 may be advanced into an aneurysm, and if the user does not believe the fit or configuration of the occlusion device 1040 within the aneurysm is desirable, the user may pull on the pusher 1056 to pull the occlusion device 1040 out of the aneurysm and into the lumen of the delivery catheter. However, then the occlusion device 1040 has been delivered into the aneurysm in an acceptable manner, the user may detach by any detachment manner (to deform, damage, or destroy the fingers 1060), via modes including but not limited to pressurized detachment, electrolytic detachment mechanisms, hydraulic detachment mechanisms, mechanical or interlocking detachment mechanisms, chemical detachment mechanisms, heat-activated detachment systems, or frictional detachment systems. In one embodiment, mechanical detachment is achieved by pushing the distal end of the microcatheter against the proximal end 1054 of the mesh cover 1042 while pulling on the pusher 1056, thus bending the fingers 1060, and removing the pusher 1056 from the occlusion device 1040. The internal tube 1046 provides for a smooth proximal end 1054 of the mesh cover 1042, and thus no remnant wire protruding proximally. Remnant protruding wires could cause thrombosis, which may cause embolic stroke. In some embodiments, the distal end 1058 of the pusher 1056 may taper down to as small as 0.001 inch or 0.002 inch, for example, if the distal end 1058 comprises a stainless steel wire. The internal tube 1046 may comprise a polyimide tube, and may have an internal diameter as small as 0.002 inch to 0.010 inch and an outer diameter of between about 0.003 inch and about 0.014 inch. In some embodiments there may be two fingers 1060, or three fingers 1060, or four fingers 1060, or five fingers 1060, of six fingers, 1060, or more.

The flush or adjacent relation of the proximal end 1052 of the internal tube 1046 to a proximal end 1054 of the mesh cover 1042 assures that there is no detachment remnant extending substantially proximal to the proximal end 1054 of the mesh cover 1042 (and into the parent artery). Thus, any potentially related thromboembolic events may be avoided, in cases wherein such a remnant would be a risk.

While the foregoing is directed to embodiments of the present disclosure, other and further embodiments may be devised without departing from the basic scope thereof. The filament diameter of the filaments comprising any of the mesh material (e.g., mesh tube including inverted mesh tubes) described herein may be between about 0.0004 inch and about 0.003 inch, or between about 0.0005 inch and about 0.002 inch, or between about 0.0006 inch and about 0.002 inch, or between about 0.0006 inch and about 0.0015 inch. The drawn filled tubes (DFT) may comprise between 0% and 100% of the total strands/filaments in any of the braided/mesh tubes. In some embodiments, the drawn filled tubes (DFT) comprise about 50% to about 100% of the total filaments of the cover and about 50% to about 100% of the total filaments of each of the doubled-over or looped tubular mesh. The radiopaque core of each of at least some of the drawn filled tubes has a cross-sectional area that is between about 10% and about 70% of the total cross-sectional area of the each of at least some of the drawn filled tubes, or between about 51% and about 70% of the total cross-sectional area of the each of at least some of the drawn filled tubes. In some embodiments, NiTi #1-DFT® wire produced by Fort Wayne Metals Research Products Corp. (Fort Wayne, Ind. USA) may be utilized. The filaments may be braided with patterns having filament crossings that are in any one or more of the following ratios of filaments: 1×1, 1×2, 2×1, 2×2, 2×3, 3×2, 3×3, etc. (e.g., warp and weft). Any low, moderate, or high pick counts may be used, for example, between about 15 picks per inch and about 300 picks per inch, or between about 20 picks per inch and about 160 picks per inch. Any of the filaments or any of the portion of the occlusion devices may be coated with compounds that enhance endothelialization, thus improving the healing process when implanted within the aneurysm, and optimizing occlusion. The pusher and occlusion device configurations presented herein may also be used for in other types of implantable devices, such as stents, flow diversion devices, filters, and occlusion devices for structural heart defects.

Additional materials may be carried on a proximal portion of the occlusion device, and configured to face opposite the aneurysm neck. In some embodiments, the material on the occlusion device may comprise a biological layer, configured to encourage growth. In some embodiments, the biological layer may comprise antibodies, in order to accelerate the formation of an endothelial layer, for example, by attracting endothelial progenitor cells (EPCs). In some embodiments, the biological layer may comprise a natural membrane or structure, such as a membrane, such as a membrane from an ear, or a cornea, or an ultra-thin piece of ligament, or even a piece of blood vessel wall. In some embodiments, the material on the occlusion device may comprise a polymer layer configured to act as a simulated arterial wall. In some embodiments, the polymer layer may comprise polytetrafluoroethylene, such as expanded polytetrafluoroethylene (ePTFE), such as that used in grafts.

The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

For purposes of the present disclosure and appended claims, the conjunction "or" is to be construed inclusively (e.g., "an apple or an orange" would be interpreted as "an apple, or an orange, or both"; e.g., "an apple, an orange, or an avocado" would be interpreted as "an apple, or an orange, or an avocado, or any two, or all three"), unless: (i) it is explicitly stated otherwise, e.g., by use of "either . . . or," "only one of," or similar language; or (ii) two or more of the listed alternatives are mutually exclusive within the particular context, in which case "or" would encompass only those combinations involving non-mutually-exclusive alternatives. For purposes of the present disclosure and appended claims, the words "comprising," "including," "having," and variants thereof, wherever they appear, shall be construed as open-ended terminology, with the same meaning as if the phrase "at least" were appended after each instance thereof

What is claimed is:

1. A method of deploying an expandable implant comprising:
    providing an implantable vaso-occlusion device comprising a mesh portion having a collapsed configuration for endovascular delivery in a subject through a delivery lumen of a delivery catheter and out of the delivery lumen along a delivery axis toward a vascular abnormality having a non-spherical shape, the mesh portion further having an expanded configuration for deployment within the vascular abnormality, the mesh portion in its expanded configuration comprising an asymmetric shape in relation to the delivery axis;
    delivering the vaso-occlusion device with the mesh portion in its collapsed configuration through the lumen of the delivery catheter toward the vascular abnormality;
    deploying the vaso-occlusion device out of the delivery lumen of the delivery catheter and into the vascular abnormality while allowing the mesh portion of the vaso-occlusion device to expand toward its expanded configuration such that the mesh portion of the vaso-occlusion device is matchingly oriented with the vascular abnormality; and removing the delivery catheter from the subject.

2. The method of claim 1, wherein a distal portion of the delivery lumen of the delivery catheter is configured to rotationally orient the vaso-occlusion device with the mesh portion is in its collapsed configuration.

3. The method of claim 2, wherein the distal portion of the delivery lumen of the delivery catheter comprises a non-circular cross-section.

4. The method of claim 3, wherein the mesh portion of the vaso-occlusion device in its collapsed configuration is configured to engage the non-circular cross-section of the delivery lumen in a keyed manner.

5. The method of claim 4, wherein the keyed manner maintains a particular rotational position of the mesh portion of the vaso-occlusion device in relation to the delivery axis.

6. The method of claim 3, wherein the non-circular cross-section comprises a shape selected from the list consisting of: an oval, an ellipse, a dogbone shape, a guitar shape, and a polygonal shape.

7. The method of claim 1, further comprising providing an elongate pusher configured for longitudinal movement within the delivery lumen of the delivery catheter and having a distal portion, the distal portion of the pusher releasably coupled to the vaso-occlusion device.

8. The method of claim 7, wherein the distal portion of the pusher is releasably coupled to the vaso-occlusion device at a releasable joint.

9. The method of claim 8, wherein the distal portion of the pusher extends from the releasable joint along a distal pusher axis.

10. The method of claim 9, wherein the mesh portion of the vaso-occlusion device comprises a concavity arranged generally around a longitudinal axis, and wherein the distal pusher axis extends from the releasable joint at an angle formed with the longitudinal axis of between about 30 degrees and about 120 degrees.

11. The method of claim 9, wherein the releasable joint is at a location on the vaso-occlusion device that is radially offset from the longitudinal axis.

12. The method of claim 11, wherein the mesh portion of the vaso-occlusion device in its expanded configuration has a maximum radius, and wherein the location of the releasable joint on the vaso-occlusion device is radially offset from the longitudinal axis at least 10% of the maximum radius.

13. The method of claim 11, wherein the mesh portion of the vaso-occlusion device in its expanded configuration has a maximum radius, and wherein the location of the releasable joint on the vaso-occlusion device is radially offset from the longitudinal axis at least 50% of the maximum radius.

14. The method of claim 8, further comprising causing the distal portion of the pusher to detach from the vaso-occlusion device at the releasable joint.

15. The method of claim 1, wherein the mesh portion comprises a plurality of filaments.

16. The method of claim 15, wherein the plurality of filaments comprises filaments comprising drawn filled tubes.

17. A method of deploying an expandable implant comprising:
providing a system comprising a delivery catheter having a delivery lumen and an elongate pusher configured for longitudinal movement within the delivery lumen of the delivery catheter, a distal portion of the pusher configured to couple to a vaso-occlusion device, the system configured to control a rotational orientation of the vaso-occlusion device with respect to a non-spherical vascular abnormality of a subject while engaged with the vaso-occlusion device, the vaso-occlusion device comprising a mesh portion having a collapsed configuration with a shape that is arranged generally around a longitudinal axis and comprising an expanded configuration with an asymmetric shape in relation to the longitudinal axis;
delivering the vaso-occlusion device with the mesh portion in its collapsed configuration through the lumen of the delivery catheter toward the vascular abnormality;
deploying the vaso-occlusion device out of the lumen of the delivery catheter and into the vascular abnormality while allowing the mesh portion of the vaso-occlusion device to expand toward its expanded configuration as the system controls the rotational orientation of the mesh portion of the vaso-occlusion device with respect to the vascular abnormality; and
removing the system from the subject.

18. The method of claim 17, wherein a distal portion of the delivery lumen of the delivery catheter is configured to rotationally orient the vaso-occlusion device with the mesh portion in its collapsed configuration, and wherein the distal portion of the delivery lumen comprises a non-circular cross-section.

19. The method of claim 17, wherein the distal portion of the pusher is coupled to the vaso-occlusion device at a releasable joint, and wherein the distal portion of the pusher extends from the releasable joint at an angle formed with the longitudinal axis of between about 30 degrees and about 120 degrees.

20. The method of claim 17, wherein the distal portion of the pusher is coupled to the vaso-occlusion device at a releasable joint, and wherein the releasable joint is at a location on the vaso-occlusive device that is radially offset from the longitudinal axis.

* * * * *